United States Patent
Nakasuji et al.

(10) Patent No.: US 12,427,493 B2
(45) Date of Patent: Sep. 30, 2025

(54) CHEMICAL REACTION METHOD, CHEMICAL REACTION APPARATUS AND PRODUCTION METHOD

(71) Applicant: Sumitomo Chemical Company, Limited, Tokyo (JP)

(72) Inventors: Takehiro Nakasuji, Ichihara (JP); Tetsuya Suzuta, Niihama (JP); Masato Matsuda, Niihama (JP); Yuichi Sato, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 464 days.

(21) Appl. No.: 18/023,464

(22) PCT Filed: Aug. 30, 2021

(86) PCT No.: PCT/JP2021/031681
§ 371 (c)(1),
(2) Date: Feb. 27, 2023

(87) PCT Pub. No.: WO2022/045326
PCT Pub. Date: Mar. 3, 2022

(65) Prior Publication Data
US 2023/0311092 A1    Oct. 5, 2023

(30) Foreign Application Priority Data
Aug. 31, 2020 (JP) .................................. 2020-145863

(51) Int. Cl.
*B01J 19/24* (2006.01)
*C07C 29/152* (2006.01)
*C07C 31/04* (2006.01)

(52) U.S. Cl.
CPC ............ *B01J 19/244* (2013.01); *C07C 29/152* (2013.01); *C07C 31/04* (2013.01); *B01J 2219/00054* (2013.01)

(58) Field of Classification Search
CPC ...... C07C 29/152; C07C 31/04; B01J 19/244; B01J 2219/00054; B01J 2208/065;
(Continued)

(56) References Cited

U.S. PATENT DOCUMENTS

2006/0074133 A1    4/2006  Fitzpatrick
2010/0267848 A1    10/2010 Duwig et al.
(Continued)

FOREIGN PATENT DOCUMENTS

CN         1741978 A       3/2006
CN         101959586 A     1/2011
(Continued)

OTHER PUBLICATIONS

Extended European Search Report issued Aug. 25, 2023 in EP Application No. 23171663.0.
(Continued)

*Primary Examiner* — Jafar F Parsa
(74) *Attorney, Agent, or Firm* — Panitch Schwarze Belisario & Nadel LLP

(57) ABSTRACT

In a chemical reaction device that improves a yield of a product and that causes a reaction, progress of which in a gaseous phase is restricted by a chemical equilibrium between a source material and the product, a cumulative value is not less than 500 mm$^2$, the cumulative value being obtained by cumulatively adding, from one end to the other end of a cooling surface in a height direction, products of (i) a distance L between (a) a surface of a catalyst layer which surface is in contact with a transmission wall and (b) an outer surface of the cooling surface and (ii) a height H of the (Continued)

catalyst layer corresponding to the outer surface having the distance L.

17 Claims, 7 Drawing Sheets

(58) Field of Classification Search
CPC ........ B01J 8/0221; B01J 8/0285; B01J 8/067;
B01J 12/00; B01J 19/2475
See application file for complete search history.

(56) References Cited

U.S. PATENT DOCUMENTS

| | | |
|---|---|---|
| 2010/0305222 A1 | 12/2010 | Thorhauge |
| 2010/0312021 A1 | 12/2010 | Thorhauge |
| 2012/0269697 A1 | 10/2012 | Thorhauge |
| 2012/0308442 A1 | 12/2012 | Duwig et al. |
| 2021/0154634 A1 | 5/2021 | Baldauf et al. |
| 2021/0245129 A1 | 8/2021 | Schuhbauer et al. |
| 2022/0363617 A1* | 11/2022 | Suzuta .................. B01J 8/0285 |

FOREIGN PATENT DOCUMENTS

| | | |
|---|---|---|
| EP | 0027329 A1 | 4/1981 |
| EP | 3556460 A1 | 10/2019 |
| JP | 2001009265 A | 1/2001 |
| JP | 2004299924 A | 10/2004 |
| JP | 2005298413 A | 10/2005 |
| JP | 2010-013422 A | 1/2010 |
| WO | 2015030578 A1 | 3/2015 |
| WO | 2019233673 A1 | 12/2019 |
| WO | 2021060145 A1 | 4/2021 |

OTHER PUBLICATIONS

Haut et al., "Development and analysis of a multifunctional reactor for equilibrium reactions: benzene hydrogenation and methanol synthesis," Chemical Engineering and Processing, vol. 43, No. 8, pp. 979-986 (2004).
International Search Report issued Oct. 19, 2021 in International Application No. PCT/JP2021/031681.
International Preliminary Report on Patentability issued Oct. 19, 2021 in International Application No. PCT/JP2021/031681.
Office Action issued Mar. 8, 2024 in CL Application No. 202300569.
Chang et al., "Coal-based syngas to methanol process," China Science and Technology Information, pp. 60-61 (2019).
Office Action issued Mar. 29, 2024 in CN Application No. 202180052217.5.

* cited by examiner

CHEMICAL REACTION METHOD, CHEMICAL REACTION APPARATUS AND PRODUCTION METHOD

CROSS-REFERENCE TO RELATED APPLICATIONS

This application is a Section 371 of International Application No. PCT/JP2021/031681, filed Aug. 30, 2021, which was published in the Japanese language on Mar. 3, 2022 under International Publication No. WO 2022/045326 A1, which claims priority under 35 U.S.C. § 119(b) to Japanese Application No. 2020-145863, filed Aug. 31, 2020, the disclosures of which are incorporated herein by reference in their entireties.

TECHNICAL FIELD

The present invention relates to a chemical reaction device and a chemical reaction method each causing a chemical reaction for obtaining a product from a source material gas to proceed in a gaseous phase with use of a catalyst.

BACKGROUND ART

Patent Literature 1 discloses (i) a method for synthesizing methanol by causing a source material gas, which contains hydrogen and carbon monoxide or carbon dioxide as main components, to react in the presence of a catalyst, and (ii) a device for the method. In the method, methanol liquefied on a cooling surface is taken out of a reaction system so that a methanol synthesis reaction exceeding an equilibrium conversion rate proceeds.

CITATION LIST

Patent Literature

[Patent Literature 1]
Japanese Patent Application Publication, Tokukai, No. 2005-298413 (Publication date: Oct. 27, 2005)

SUMMARY OF INVENTION

Technical Problem

In a reaction method that causes a reaction to proceed in a gaseous phase with use of a catalyst, including a reaction method with use of a reaction device as disclosed in Patent Literature 1, it is known that changing condition parameters such as a pressure in a reaction system, a temperature in the reaction system, and a ratio (W/F) between a catalyst amount and a source material feed rate in the reaction system contributes to a reaction yield of a product.

An aspect of the present invention has an object to provide a chemical reaction method and a chemical reaction device each of which improves a yield of a product by changing an internal structure of a reaction device, without changing the above condition parameters.

Solution to Problem

In order to attain the object, a chemical reaction method in accordance with an aspect of the present invention is a chemical reaction method that causes a reaction, a product of which contains a component having a boiling point higher than a component of a source material gas, and progress of which in a gaseous phase is restricted by a chemical equilibrium between a source material and the product, to proceed, wherein a chemical reaction device including: a catalyst layer which contains a catalyst that promotes the reaction; a cooling surface which is provided apart from the catalyst layer with a space between the cooling surface and the catalyst layer, which is maintained at a temperature not higher than a dew point of a reactant gas produced by the reaction, and which extends in a predetermined direction; and a transmission wall which is provided at a boundary between the catalyst layer and the space and which allows the reactant gas to pass therethrough, a cumulative value being not less than 500 $mm^2$, the cumulative value being obtained by cumulatively adding, from one end to the other end of the cooling surface in the predetermined direction, products of (i) a distance between (a) a surface of the catalyst layer which surface is in contact with the transmission wall and (b) the cooling surface and (ii) a height of the catalyst layer corresponding to the cooling surface having the distance, is used to cause a chemical reaction to proceed by supplying the source material gas to the catalyst layer, and to condense, on the cooling surface and in the space, some of a product produced by the chemical reaction.

A chemical reaction device in accordance with an aspect of the present invention is a chemical reaction device that causes a reaction, a product of which contains a component having a boiling point higher than a component of a source material gas, and progress of which in a gaseous phase is restricted by a chemical equilibrium between a source material and the product, to proceed, the chemical reaction device including: a catalyst layer to which the source material gas is supplied and which contains a catalyst that promotes the reaction; a cooling surface which is provided apart from the catalyst layer with a space between the cooling surface and the catalyst layer, which is maintained at a temperature not higher than a dew point of the reactant gas, and which extends in a predetermined direction; and a transmission wall which is provided at a boundary between the catalyst layer and the space and which allows the reactant gas that has been produced by the reaction to pass therethrough, a cumulative value being not less than 500 $mm^2$, the cumulative value being obtained by cumulatively adding, from one end to the other end of the cooling surface in the predetermined direction, products of (i) a distance between (a) a surface of the catalyst layer which surface is in contact with the transmission wall and (b) an outer surface of the cooling surface and (ii) a height of the catalyst layer corresponding to the outer surface having the distance, and the chemical reaction device condensing some of a product on a surface of the cooling surface and in the space.

A chemical reaction device in accordance with an aspect of the present invention is a chemical reaction device including a reaction container including at least one reaction tube that has a multiple structure and that causes a reaction, a product of which contains a component having a boiling point higher than a component of a source material gas, and progress of which in a gaseous phase is restricted by a chemical equilibrium between a source material and the product, to proceed inside the at least one reaction tube, the at least one reaction tube each including: an inner cylinder which allows a reactant gas produced by the reaction to pass therethrough; an outer cylinder inside which the inner cylinder is provided; a cooling tube which is provided inside the inner cylinder and which extends in a predetermined direction; and a catalyst layer which is provided between the inner cylinder and the outer cylinder, a cumulative value being not less than 500 mm², the cumulative value being obtained by cumulatively adding, from one end to the other end of the cooling tube in the predetermined direction, products of (i) a distance between (a) a surface of the catalyst layer which surface is in contact with the inner cylinder and (b) an outer surface of the cooling tube and (ii) a height of the catalyst layer corresponding to the outer surface having the distance, a temperature of the outer surface of the cooling tube being maintained at a temperature not higher than a dew point of the reactant gas, and the chemical reaction device condensing some of the product in a space provided between the cooling tube and the inner cylinder.

A chemical reaction device in accordance with an aspect of the present invention is a chemical reaction device including a reaction container including at least one reaction tube that has a multiple structure and that causes a reaction, a product of which contains a component having a boiling point higher than a component of a source material gas, and progress of which in a gaseous phase is restricted by a chemical equilibrium between a source material and the product, to proceed inside the at least one reaction tube, the at least one reaction tube each including: an inner cylinder which allows a reactant gas produced by the reaction to pass therethrough; an outer cylinder inside which the inner cylinder is provided and which extends in a predetermined direction; and a catalyst layer which is provided inside the inner cylinder, a cumulative value being not less than 500 mm², the cumulative value being obtained by cumulatively adding, from one end to the other end of an inner surface of the outer cylinder in the predetermined direction, products of (i) a distance between (a) a surface of the catalyst layer which surface is in contact with the inner cylinder and (b) the inner surface and (ii) a height of the catalyst layer corresponding to the inner surface having the distance, a temperature of the inner surface of the outer cylinder being maintained at a temperature not higher than a dew point of the reactant gas, and the chemical reaction device condensing some of the product in a space provided between the outer cylinder and the inner cylinder.

A methanol production method in accordance with an aspect of the present invention is a methanol production method that causes a reaction, a product of which contains a component having a boiling point higher than a component of a source material gas, and progress of which in a gaseous phase is restricted by a chemical equilibrium between a source material and the product, to proceed, wherein a chemical reaction device containing carbon oxide and hydrogen as the source material gas, the chemical reaction device including: a catalyst layer which contains a catalyst for methanol synthesis; a cooling surface which is provided apart from the catalyst layer with a space between the cooling surface and the catalyst layer, which is maintained at a temperature not higher than a dew point of a reactant gas produced by the reaction, and which extends in a predetermined direction; and a transmission wall which is provided at a boundary between the catalyst layer and the space and which allows the reactant gas to pass therethrough, a cumulative value being not less than 500 mm², the cumulative value being obtained by cumulatively adding, from one end to the other end of the cooling surface in the predetermined direction, products of (i) a distance between (a) a surface of the catalyst layer which surface is in contact with the transmission wall and (b) the cooling surface and (ii) a height of the catalyst layer corresponding to the cooling surface having the distance, is used to cause a chemical reaction to proceed by supplying the source material gas to the catalyst layer, and to condense, on the cooling surface and in the space, some of a reactant gas produced by the chemical reaction.

Advantageous Effects of Invention

An aspect of the present invention makes it possible to improve a yield of a product by changing an internal structure of a reaction device that causes a reaction, progress of which in a gaseous phase is restricted by a chemical equilibrium between a source material and the product, to proceed.

DESCRIPTION OF EMBODIMENTS

Embodiment 1

(Configuration of Reaction Device 100)

Figure 1:
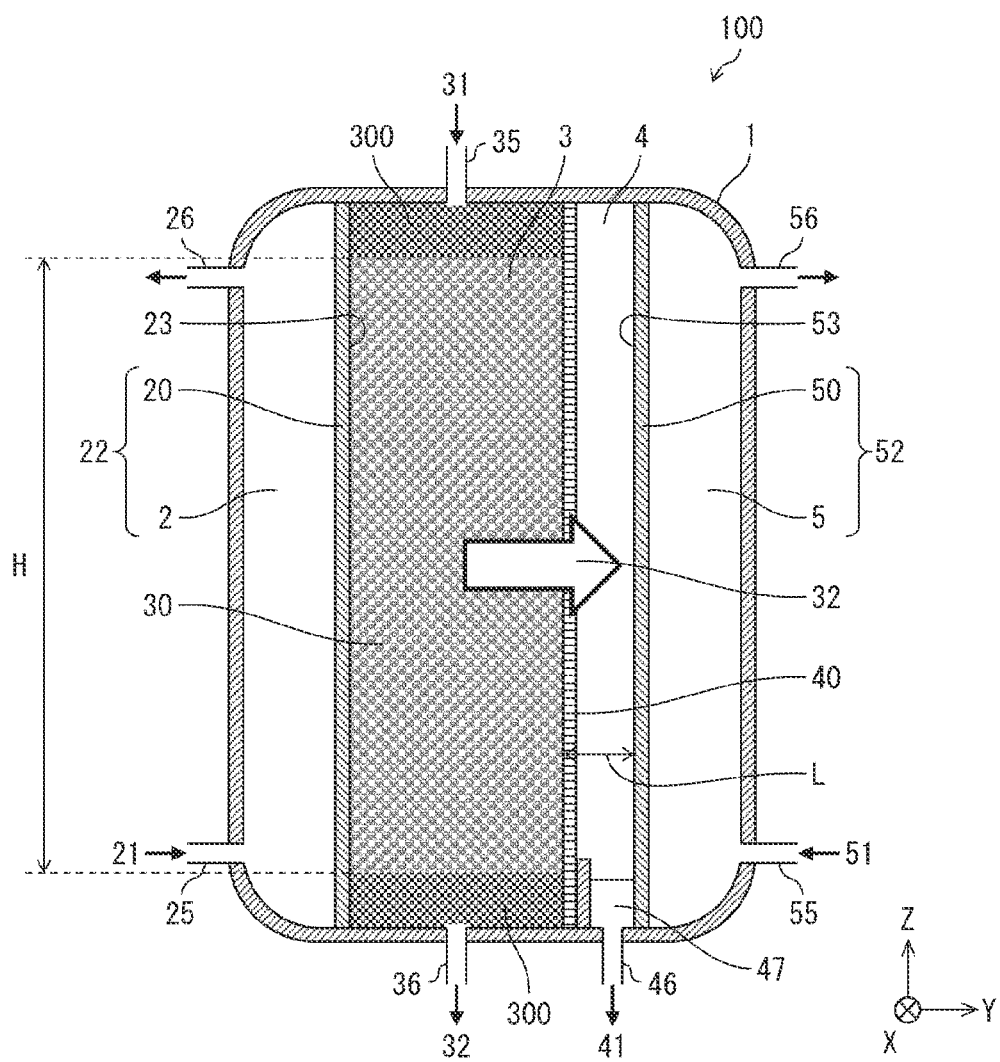
FIG. 1 is a cross-sectional view of a reaction device in accordance with Embodiment 1.

The following description will discuss an embodiment of the present invention in detail. FIG. 1 is a cross-sectional view of a reaction device 100 (chemical reaction device) in accordance with Embodiment 1, the cross-sectional view being taken along a plane perpendicular to a bottom surface of the reaction device 100. The reaction device 100 is a chemical reaction device that causes a reaction, a product of which contains a component having a boiling point higher than a main component of a source material gas 31, and progress of which in a gaseous phase is restricted by a chemical equilibrium between a source material and the product, to proceed. Note that the X-axis, the Y-axis, and the Z-axis in the drawings define directions in a three-dimensional space in each of the drawings. The term "height" as used herein corresponds to the length in the Z-axis direction in the drawings. Hereinafter, a direction in which each of the X-axis, the Y-axis, and the Z-axis extends is herein constant.

In the reaction device 100, the product is condensed and collected out of a reaction container. This causes the chemical equilibrium to be shifted toward the product and thus enables the reaction to proceed. In particular, the reaction device 100 can be suitably used as a device for carrying out chemical reactions which are represented by the respective following formulas (1) to (3), in which the source material gas 31 contains a carbon oxide and hydrogen, and the product of which contains methanol.

$$CO + 2H_2 \leftrightarrow CH_3OH \quad (1)$$

$$CO_2 + 3H_2 \leftrightarrow CH_3OH + H_2O \quad (2)$$

$$CO_2 + H_2 \leftrightarrow CO + H_2O \quad (3)$$

In a case where methanol is produced by the chemical reactions represented by the respective above formulas (1) to (3), a catalyst containing copper and zinc can be used as a catalyst for methanol synthesis (catalyst 30 described below in detail). Examples of the carbon oxide used in the chemical reactions include carbon dioxide and carbon monoxide. In the chemical reactions, a gas containing hydrogen and at least one kind selected from the group consisting of carbon dioxide and carbon monoxide can be used as the source material gas.

The reaction device 100 can be used not only for the above-described reactions by which methanol is synthesized but for carrying out a reaction that yields dimethyl ether or ammonia as a product.

As illustrated in FIG. 1, the reaction device 100 includes a reaction container 1, a first heat exchange section 22, a catalyst layer 3 that is in contact with the first heat exchange section 22, a transmission wall 40, and a second heat exchange section 52 that is provided apart from the transmission wall 40 with a space 4 between the second heat exchange section 52 and the transmission wall 40. The transmission wall 40 is provided on a side of the catalyst layer 3 which side faces away from the first heat exchange section 22. The reaction container 1 is, for example, a metallic container made of pressure-resistant stainless steel.

The first heat exchange section 22 is a heat exchanger that is constituted by an inner wall surface of the reaction container 1 and a first heat exchange wall 20 and that has a heat transfer surface 23 on the catalyst layer 3 side. Inside the first heat exchange section 22, a first heating medium region 2 is provided through which a first heating medium 21 flows. The first heat exchange section 22 is provided with (i) a first heating medium feed opening 25 through which the first heating medium 21 is to be supplied to the first heating medium region 2 and (ii) a first heating medium collection opening 26 through which the first heating medium 21 is to be discharged from the first heating medium region 2. The first heat exchange wall 20 is made of a member that does not allow any fluid to pass therethrough. The heat transfer surface 23 of the first heat exchange wall 20 acts as a first heat exchange surface. In FIG. 1, the first heat exchange wall 20 is illustrated as a plate-like member. Note, however, that the first heat exchange wall 20 may have a shape which is not limited to a plate-like shape. The first heat exchange wall 20 may have a surface formed into a wavy shape or the like. The first heat exchange section 22 may also have a shape that is not limited to the shape illustrated in FIG. 1 but may be any of various shapes which allow an increase in efficiency of heat exchange, such as a multi-pipe configuration and a spiral shape.

The first heat exchange section 22 can maintain the heat transfer surface 23 at a temperature higher than a dew point of a reactant gas 32 by allowing the first heating medium 21 to flow through the first heating medium region 2. In a case where a reaction that occurs in the catalyst layer 3 is an exothermic reaction, the first heating medium 21 acts as a heating medium for cooling heat of reaction which heat is generated by the exothermic reaction. In a case where the reaction that occurs in the catalyst layer 3 is an endothermic reaction, the catalyst layer 3 is maintained at a temperature not lower than the dew point of the reactant gas 32 by the first heating medium acting as a heating medium for heating the catalyst layer 3.

Note that the wording "dew point of the reactant gas 32" means a temperature at which condensation starts in a case where the reactant gas 32 is cooled in a state where a reaction in a gaseous phase has reached a chemical equilibrium at a temperature and a pressure at which the reactant gas 32 is present in the catalyst layer 3.

In a case where a composition of the gaseous phase and the pressure are given, the dew point of the reactant gas 32 can be calculated simultaneously with a composition of a condensate by using a vapor-liquid equilibrium model to carry out an appropriate vapor-liquid equilibrium calculation. In a case where the pressure is a high pressure exceeding 1 MPa, the vapor-liquid equilibrium model can be, for example, an extended cubic equation of state such as Peng-Robinson equation or Redlich-Kwong-Soave equation.

The heat transfer surface 23 more preferably has a temperature that allows the catalyst layer 3 as a whole to be maintained at a temperature higher than the dew point of the reactant gas 32. The reaction device 100 that includes the heat transfer surface 23 can maintain the catalyst layer 3 at a temperature suitable for the reaction. This allows an increase in efficiency of the reaction. In a case where the product is methanol, examples of the first heating medium 21 include high-pressure boiler water (e.g. saturated water at 2.2 MPaG to 5.0 MPaG) at 220° C. to 265° C., a molten metal salt (e.g. a mixture of sodium nitrite and potassium nitrate), and heat transfer oil. Note that numerical expressions such as "A to B" herein mean "not less than A and not more than B".

The second heat exchange section 52 is a heat exchanger that is constituted by an inner wall surface of the reaction container 1 and a second heat exchange wall 50. Inside the second heat exchange section 52, a second heating medium region 5 is provided through which a second heating medium 51 flows. The second heat exchange section 52 is provided with (i) a second heating medium feed opening 55 through which the second heating medium 51 is to be supplied to the second heating medium region 5 and (ii) a second heating medium collection opening 56 through which the second heating medium 51 is to be discharged from the second heating medium region 5. The second heat exchange wall 50 is made of a member that does not allow any fluid to pass therethrough. The second heat exchange section 52 has a cooling surface 53 on the space 4 side. The cooling surface 53 extends in the Z-axis direction, and maintains a temperature not higher than the dew point of the reactant gas 32 so as to cool the reactant gas 32 in the space 4 and condense the product on a surface of the cooling surface 53 and in the space 4. In FIG. 1, the second heat exchange wall 50 is illustrated as a plate-like member. Note, however, that the second heat exchange wall 50 may have a shape which is not limited to a plate-like shape. That is, the cooling surface 53 may be formed into a wavy shape or the like. The second heat exchange section 52 may also have a shape that is not limited to the shape illustrated in FIG. 1 but may be any of various shapes which allow an increase in efficiency of heat exchange, such as a multi-pipe configuration and a spiral shape.

The second heat exchange section 52 can maintain the cooling surface 53 at a temperature not higher than the dew point of the reactant gas 32 by allowing the second heating medium 51 to flow through the second heating medium region 5. In a case where the product is methanol, examples of the second heating medium 51 include low-pressure boiler water (e.g. saturated water at −0.05 MPaG to 0.4 MPaG) at 80° C. to 150° C., cooling water (e.g. methanol water, ethylene glycol water) at −20° C. to 100° C., industrial water, an aqueous ammonia solution, a hydrocarbon compound such as pentane, and a chlorofluorocarbon compound such as 1,1,1,3,3-pentafluoropropane.

More specifically, in a case where a reaction catalyzed by the catalyst 30 is an exothermic reaction carried out at a temperature higher than the dew point of the reactant gas 32 by not less than 80° C., it is preferable that the first heating medium 21 have a temperature lower than an average temperature of the catalyst layer 3 by 5° C. to 30° C. and that the second heating medium 51 have a temperature lower than the dew point of the reactant gas 32 by not less than 20° C. Note here that the temperature of the first heating medium and the temperature of the second heating medium each mean an average of a temperature at a corresponding feed opening and a temperature at a corresponding collection opening.

Note that, in FIG. 1, the first heating medium feed opening 25 and the first heating medium collection opening 26 are provided in a lower part and an upper part, respectively, of the reaction container 1, and the second heating medium feed opening 55 and the second heating medium collection opening 56 are provided in the lower part and the upper part, respectively, of the reaction container 1. It should be understood, however, that each of the above collection openings and feed openings can be provided at an appropriate position in an appropriate manner in accordance with a pressure of a corresponding heating medium to be used. Furthermore, a temperature and a pressure at which each of the first heating medium 21 and the second heating medium 51 is supplied can be set to respective appropriate values in accordance with a temperature of the reaction carried out in the reaction container 1 and the dew point of the reactant gas 32 in the reaction container 1.

The catalyst layer 3 is filled with the catalyst 30 that is suitable for the reaction. The catalyst layer 3 is a region which contains the catalyst 30 and in which the source material gas 31 and the catalyst 30 come into contact with each other, and the reaction proceeds. The catalyst 30 can be, for example, a catalyst containing copper and zinc oxide as main components. A space between the catalyst layer 3 and the reaction container 1 may be filled with a filling 300. Furthermore, in order to support the catalyst 30, the catalyst layer 3 may have a bottom part that is provided with a supporting plate (not illustrated) made of a porous member.

Figure 2:
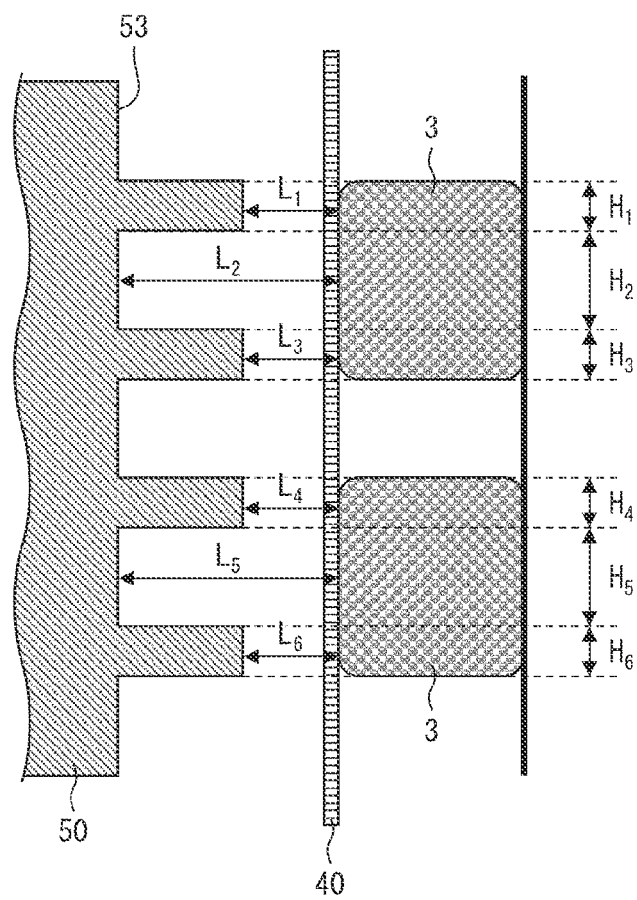
FIG. 2 is a partial cross-sectional view schematically illustrating the reaction device in accordance with Embodiment 1.

FIG. 2 is a partially enlarged cross-sectional view of the reaction device 100 in accordance with Embodiment 1, the cross-sectional view being taken along the plane perpendicular to the bottom surface of the reaction device 100. FIG. 2 shows an example of a case where a plurality of protrusions are provided in the Z-axis direction of the cooling surface 53. As illustrated in FIG. 2, the catalyst layer 3 has a height $H_x$ (x=1, 2, . . . ) corresponding to the cooling surface 53 having a distance $L_x$ (x=1, 2, . . . ). The distance $L_x$ is a distance between the cooling surface 53 and a surface of the catalyst layer 3 which surface is in contact with the transmission wall 40. Specifically, the catalyst layer 3 has a height $H_1$ corresponding to a distance $L_1$, a height $H_2$ corresponding to a distance $L_2$ . . . a height $H_n$ corresponding to a distance $L_n$. In this case, the height H of the catalyst layer 3 can be represented by a sum total of heights $H_x$ ($H_1+H_2+\ldots+H_n$). In a case where the cooling surface 53 and the surface of the catalyst layer 3 which surface is in contact with the transmission wall 40 are flat in the Z-axis direction, the distance $L_x$ is an identical distance throughout the cooling surface 53. Thus, a distance at a predetermined position in this case can be simply expressed as the distance L.

In a case where the catalyst layer 3 is configured as a collection of a plurality of non-continuous catalyst layers as illustrated in FIG. 2, the height H of the catalyst layer 3 can be represented by the sum total of the heights $H_x$ ($H_1+H_2+\ldots+H_n$).

In some cases, due to a degree of filling of the catalyst 30, an upper end surface or a lower end surface of the catalyst layer 3 is not flat, or the upper end surface and the lower end surface are not parallel to each other. In such a case, the height H of the catalyst layer 3 herein means the height of the catalyst layer 3 on a surface of the catalyst layer 3 which surface is in contact with the transmission wall 40. In a case where the surface of the catalyst layer 3 which surface is in contact with the transmission wall 40 is not flat, the distance $L_x$ and the height $H_x$ are defined as in a case where the protrusions mentioned earlier are provided on the cooling surface 53.

From the viewpoint of the amount of treatment per reaction device, the sum total of the heights $H_x$ is preferably not less than 1,000 mm. Furthermore, from an economic viewpoint, the sum total of the heights $H_x$ is preferably not more than 20,000 mm.

The transmission wall 40 is provided at a boundary between the catalyst layer 3 and the space 4, and is a member that allows the reactant gas 32 to pass therethrough. The transmission wall 40 is made of, for example, a metal member that is made of stainless steel. The transmission wall 40 is made of a member that allows the reactant gas 32 to pass therethrough but does not allow the catalyst 30 to pass therethrough. Examples of such a member include a metal mesh that has an appropriate pore size. The reactant gas 32 contains an unreacted source material gas and an uncondensed reaction product gas.

The space 4 is a space that is provided between the transmission wall 40 and the cooling surface 53. In a lower part of the space 4, a condensate storing section 47 is provided in which a product that has been condensed and liquefied on the cooling surface 53 and/or in a vicinity of the cooling surface 53 can be stored. A condensate 41 is collected through a condensate collection opening 46 that is provided in a bottom part of the condensate storing section 47.

Note here that the distance $L_x$ between the cooling surface 53 and the surface of the catalyst layer 3 which surface is in contact with the transmission wall 40 is preferably not less than 0.5 mm and not more than 500 mm. The above range of the distance $L_x$ is preferably achieved in a region of not less than 80%, and more preferably not less than 95% of a vertical length of an entire region obtained by a sum of partial regions of the cooling surface 53 which face the catalyst layer 3. The distance $L_x$ is desirably not less than 0.5 mm in order to secure a space for a condensed droplet to drop by gravity. Furthermore, the distance $L_x$ that is less than 0.5 mm may cause condensation of a product in the catalyst layer 3. In contrast, the distance $L_x$ that is more than 500 mm may increase various costs due to an increase in size of the reaction container 1. This may lead to economic inconvenience. Thus, the distance $L_x$ is preferably not less than 0.5 mm and not more than 500 mm.

(Cumulative Value)

According to the reaction device 100 of Embodiment 1, a cumulative value is not less than 500 mm², the cumulative value being obtained by cumulatively adding, from one end to the other end of the cooling surface 53 in the Z-axis direction, products of (i) the distance $L_x$ between the cooling surface 53 and the surface of the catalyst layer 3 which surface is in contact with the transmission wall 40 and (ii) the height $H_x$ of the catalyst layer 3 corresponding to the cooling surface having the distance $L_x$.

In the present invention, "a cumulative value obtained by cumulative addition from one end to the other end of the cooling surface 53 in a predetermined direction is not less than 500 mm$^2$" means that a cumulative value obtained by cumulative addition from one end to the other end of the cooling surface 53 in the Z-axis direction only needs to be not less than 500 mm$^2$ at one or more predetermined places. In a case where the cumulative value varies in value depending on a predetermined position in the X-axis direction, the cumulative value obtained by cumulative addition from one end to the other end of the cooling surface 53 in the Z-axis direction can be not less than 500 mm$^2$ in not less than 50%, preferably not less than 80%, more preferably not less than 95%, and particularly preferably 100% of a region in the X-axis direction.

According to the reaction device 100, the cumulative value obtained by cumulative addition from one end to the other end of the cooling surface 53 in the Z-axis direction is not less than 500 mm$^2$ at one or more predetermined places in the X-axis direction. Thus, as compared with a reaction device in which the cumulative value is less than 500 mm$^2$ in 100% of a region in the X-axis direction, the reaction device 100 can further improve a reaction yield of the product also in the case of using condition parameters identical to those used in the reaction device. The condition parameters include a pressure in a reaction system, a temperature in the reaction system, and a ratio (W/F) between a catalyst amount and a source material feed rate in the reaction system.

In the above reaction, in which the product is condensed and collected out of a reaction container so that the chemical equilibrium is shifted toward the product, any of (i) a reaction rate of a reaction that occurs in the catalyst layer 3, (ii) a diffusion rate at which the product diffuses toward the cooling surface 53, and (iii) a condensation rate on the cooling surface 53 governs an entire reaction rate. Increasing the distance $L_x$ is considered to reduce a driving force by which the chemical equilibrium is shifted toward the product. Thus, a change to increase the distance $L_x$ is commonly not made. However, the inventors of the present invention have found that the reaction device 100 the internal structure of which is configured such that the cumulative value is not less than 500 mm$^2$ can rather improve the reaction yield of the product.

As described earlier, from the economic viewpoint, the distance $L_x$ is preferably not more than 500 mm, and the sum total of the heights $H_x$ is preferably not more than 20,000 mm. The cumulative value is therefore preferably not more than 10,000,000 mm$^2$. Since the reaction device 100 is configured such that the cumulative value is not less than 500 mm$^2$ and not more than 10,000,000 mm$^2$, the reaction device 100 and a chemical reaction method in which the reaction device 100 is used can improve the reaction yield of the product. Furthermore, it is possible to provide the reaction device 100 and the chemical reaction method that are preferable also from the economic viewpoint.

(Flow of Reaction)

The source material gas 31 is supplied through a source material gas inlet 35 which is provided in an upper part of the catalyst layer 3, and comes into contact with the catalyst 30 which fills the catalyst layer 3, so that a reaction proceeds. The reactant gas 32 that has been produced by the reaction passes through the transmission wall 40 and travels to the space 4, and is cooled, on the cooling surface 53, to a temperature not higher than the dew point of the reactant gas 32, so that a product is condensed. The product that has been condensed and liquefied drops into the condensate storing section 47 and is collected, as the condensate 41, through the condensate collection opening 46.

The reactant gas 32 that passes through the transmission wall 40 from the catalyst layer 3 side also includes the unreacted source material gas. However, a main component contained in the unreacted source material gas is not condensed on the cooling surface 53. Furthermore, since the condensate storing section 47 is provided in the lower part of the space 4, the unreacted source material gas returns to the catalyst layer 3 instead of being discharged through the condensate collection opening 46 together with the condensate 41.

Note here that a flow rate of gas that passes through the transmission wall 40 is preferably kept in an appropriate range so that a ratio of the unreacted source material gas which passes through the space 4 and heads toward an exit of the catalyst layer 3 is not excessively high. In order to keep the flow rate of the gas in the appropriate range, it is possible to, for example, adjust a void area ratio of the porous member of which the transmission wall 40 is formed. Alternatively, in order to keep the flow rate of the gas in the appropriate range, it is possible to insert, into the space 4, a member that serves as a resistance to the flow of the gas.

The reactant gas 32 that contains the source material which has not been reacted in the catalyst layer 3 is collected through a reactant gas collection opening 36.

(Collection of Heat of Reaction and Heat of Condensation)

The first heating medium 21 is supplied, as, for example, boiler water at 2.2 MPaG to 5.0 MPaG, through the first heating medium feed opening 25. In a case where the reaction is an exothermic reaction, the heat of reaction which heat has been generated in the catalyst layer 3 is heat exchanged through the first heat exchange wall 20 and collected by the first heating medium 21. The first heating medium 21 passes through the first heating medium collection opening 26 and is collected into a high-pressure steam separator drum (not illustrated). Then, high-pressure steam obtained by gas-liquid separation is used as, for example, a power source for compressing the source material.

The second heating medium 51 is supplied, as, for example, boiler water at 0.05 MPaG, through the second heating medium feed opening 55. The second heating medium 51 collects therein heat of the reactant gas 32 by heat exchange through the second heat exchange wall 50 in order to reduce a temperature of the reactant gas 32 in the space 4 to not higher than the dew point on the surface of the cooling surface 53. The second heating medium 51 passes through the second heating medium collection opening 56 and is collected into a low-pressure steam separator drum (not illustrated). Then, low-pressure steam obtained by gas-liquid separation is used as, for example, a heat source in a step of purifying the product.

Effect of Embodiment 1

As described above, the reaction device 100 of Embodiment 1 is a chemical reaction device that causes a reaction, a product of which contains a component having a boiling point higher than a component of the source material gas 31, and progress of which in a gaseous phase is restricted by a chemical equilibrium between a source material and the product, to proceed. A chemical reaction method of Embodiment 1 is a method in which the reaction device 100 is used. The reaction device 100 includes: the catalyst layer 3 to which the source material gas 31 is supplied and which contains the catalyst 30 that promotes the reaction; the cooling surface 53 which is provided apart from the catalyst layer 3 with the space 4 between the cooling surface 53 and the catalyst layer 3, which is maintained at a temperature not higher than a dew point of the reactant gas 32, and which extends in a predetermined direction; and the transmission wall 40 which is provided at a boundary between the catalyst layer 3 and the space 4 and which allows the reactant gas 32 that has been produced by the reaction to pass therethrough. A cumulative value is not less than 500 mm², the cumulative value being obtained by cumulatively adding, from one end to the other end of the cooling surface 53 in a height direction, products of (i) the distance $L_x$ between the cooling surface 53 and the surface of the catalyst layer 3 which surface is in contact with the transmission wall 40 and (ii) the height $H_x$ of the catalyst layer corresponding to the cooling surface 53 having the distance $L_x$. The reaction device 100 condenses some of the product on the surface of the cooling surface 53 and in the space 4.

According to the reaction device 100 and the chemical reaction method in which the reaction device 100 is used, the product is collected, as the condensate 41, out of the reaction container 1. This allows a reaction in a reaction system, in which progress of the reaction in a gaseous phase is restricted by a chemical equilibrium, to proceed beyond an equilibrium conversion rate.

Furthermore, according to the reaction device 100, the cumulative value obtained by cumulative addition from one end to the other end of the cooling surface 53 in the Z-axis direction is not less than 500 mm² at one or more predetermined places in the X-axis direction. Thus, the reaction device 100 and the chemical reaction method in which the reaction device 100 is used can improve a reaction yield of the product also in the case of using condition parameters identical to those used in a reaction device in which the cumulative value is less than 500 mm² in 100% of a region in the X-axis direction.

In the reaction device 100 and the chemical reaction method in which the reaction device 100 is used, it is possible to improve a reaction yield of methanol according to a methanol production method in which a carbon oxide and hydrogen are contained as the source material gas 31 and a catalyst for methanol synthesis is used as the catalyst 30.

Embodiment 2

The following description will discuss another embodiment of the present invention. Note that for convenience, members having functions identical to those of the respective members described in Embodiment 1 are given respective identical reference numerals, and a description of those members is omitted.

Figure 3:
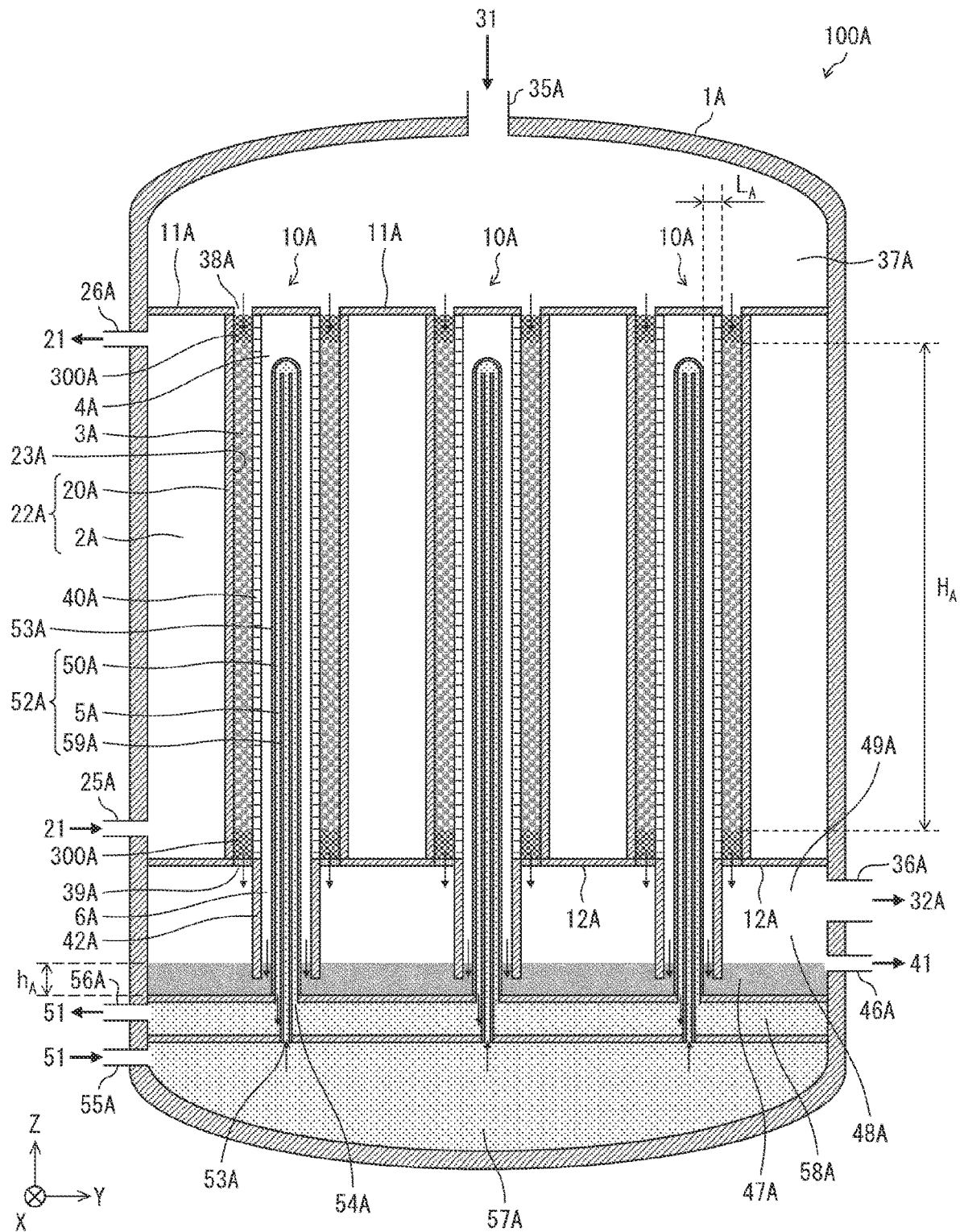
FIG. 3 is a cross-sectional view of a reaction device in accordance with Embodiment 2.
Figure 4:
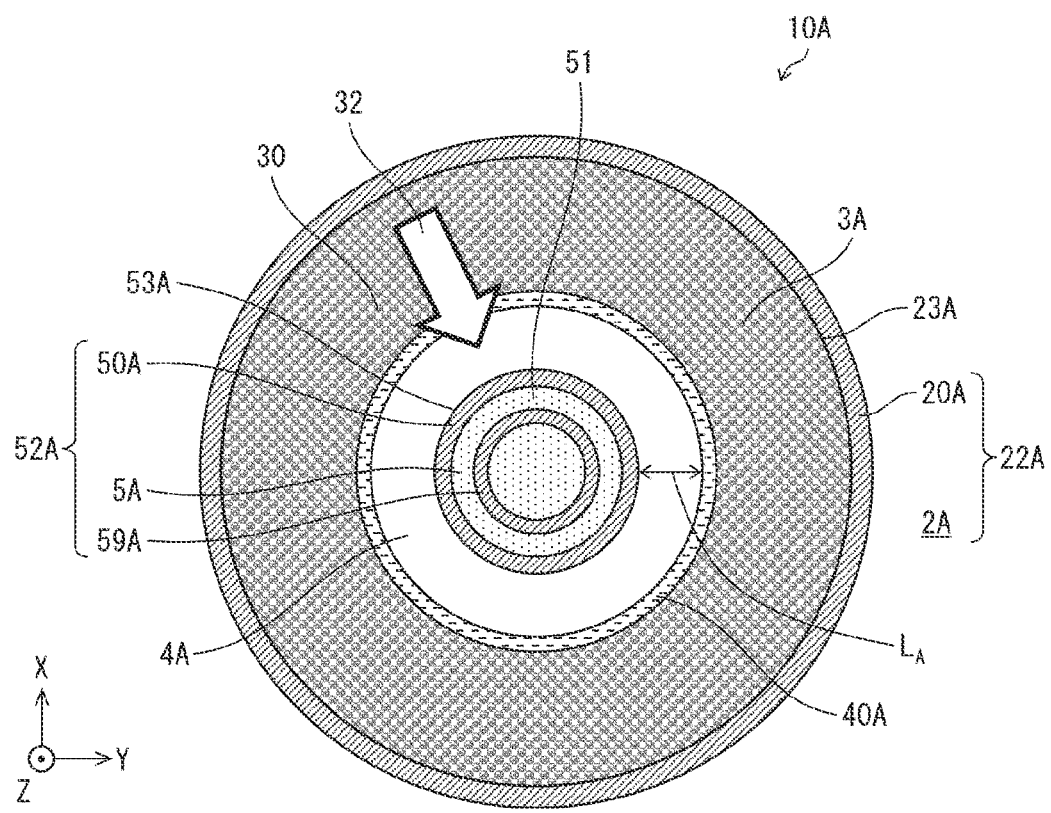
FIG. 4 is a cross-sectional view of a reaction tube included in the reaction device in accordance with Embodiment 2.

FIG. 3 is a cross-sectional view of a reaction device 100A in accordance with Embodiment 2, the cross-sectional view being taken along a plane perpendicular to a bottom surface of the reaction device 100A. FIG. 4 is a cross-sectional view of a reaction tube 10A included in the reaction device 100A, the cross-sectional view being taken along a plane perpendicular to a long axis of the reaction tube 10A. The reaction device 100A has a basic principle identical to that of the reaction device 100. The reaction device 100A differs from the reaction device 100 in that cylindrical reaction tubes are used in the reaction device 100A.

As in the case of the reaction device 100, the reaction device 100A can be suitably used as a device for carrying out a chemical reaction in which a source material gas 31 contains a carbon oxide and hydrogen and a product of which contains methanol. In addition, the reaction device 100A can be used also for carrying out a reaction that yields dimethyl ether or ammonia as a product.

In the source material gas 31, impurities, examples of which are listed below, are preferably reduced to an extent that do not excessively affect methanol production. Examples of the impurities include sulfur compounds and sulfur elements (e.g. hydrogen sulfide, carbonyl sulfide, carbon disulfide, sulfur oxide, thiophene, and methyl thiocyanate), halogen compounds and halogen elements (e.g. hydrogen chloride and hydrocarbon chloride), metal carbonyls (e.g. Fe carbonyl and Ni carbonyl), metallic compounds (e.g. metallic compounds containing vanadium and alkali metals), nitrogen compounds (e.g. ammonia, amine, nitrogen oxide, nitrile, and hydrogen cyanide), substances in liquid form and solid form (e.g. tar, carbon black, soot, ash, fine metal powder), and unsaturated hydrocarbons. The catalyst 30 is not particularly limited provided that the catalyst 30 is a catalyst for promoting the reaction. Note, however, that the catalyst 30 may be a catalyst containing Cu and/or Zn, or may be a catalyst further containing Al, Mg, Cr, Mn, V, Ti, Zr, Ta, Mo, W, Si, a rare earth, Ga, or the like.

(Reaction Device 100A)

As illustrated in FIG. 3, the reaction device 100A includes a plurality of reaction tubes 10A that are provided inside a reaction container 1A and that extend in the Z-axis direction. The number of the reaction tubes 10A that are provided inside the reaction container 1A is not particularly limited, provided that the number is at least one. In consideration of reaction efficiency, the number of the reaction tubes 10A is preferably more than one. On an upper side of the plurality of reaction tubes 10A, a source material gas supplying section 37A is provided which is filled with the source material gas 31 to be supplied to each of the reaction tubes 10A. On a lower side of the plurality of reaction tubes 10A, a storing section 48A is provided which stores therein a liquid that has been condensed inside each of the reaction tubes 10A and gas that has passed through a catalyst layer 3A. On a lower side of the storing section 48A, a second heating medium collecting section 58A is provided which stores therein a second heating medium 51 that has been discharged from a second heat exchange section 52A (cooling tube, described later). Furthermore, on a lower side of the second heating medium collecting section 58A, a second heating medium supplying section 57A is provided which stores therein the second heating medium 51 to be supplied to the second heat exchange section 52A. The above sections are formed by using a metal plate (e.g. a plate made of stainless steel) to partition an internal space of the reaction container 1A.

A reaction tube 10A is open to (i) a metal plate 11A that is located in an upper part of the reaction tube 10A and (ii) a metal plate 12A that is located in a lower part of the reaction tube 10A. An outer cylinder 20A of the reaction tube 10A is joined to the metal plates 11A and 12A by welding.

As illustrated in FIGS. 2 and 4, the reaction tube 10A includes, in this order from outside, the outer cylinder 20A, the catalyst layer 3A that has a cylindrical shape and is in contact with an inner wall surface of the outer cylinder 20A, an inner cylinder 40A that is provided on an inner side of the catalyst layer 3A, and the second heat exchange section 52A (cooling tube). The second heat exchange section 52A is provided apart from the inner cylinder 40A with a space 4A (first space) between the second heat exchange section 52A and the inner cylinder 40A.

A first heat exchange section 22A is a heat exchanger that is constituted by (i) some of an inner wall surface of the reaction container 1A, (ii) an outer wall surface of the outer cylinder 20A, and (iii) the metal plates 11A and 12A and that has a heat transfer surface 23A on the catalyst layer 3A side. Inside the first heat exchange section 22A, a first heating medium region 2A is provided which is common among the plurality of reaction tubes 10A. Through the first heating medium region 2A, a first heating medium 21 (heating medium) flows. The first heating medium 21 is a heating medium for maintaining the outer cylinder 20A at a temperature higher than a dew point of a reactant gas 32. The outer cylinder 20A is made of a member that does not allow any fluid to pass therethrough. The heat transfer surface 23A of the outer cylinder 20A acts as a first heat exchange surface.

The reaction container 1A has a side wall that is provided with (i) a first heating medium feed opening 25A through which the first heating medium 21 is to be supplied to the first heating medium region 2A and (ii) a first heating medium collection opening 26A through which the first heating medium 21 is to be discharged from the first heating medium region 2A. The first heat exchange section 22A can maintain the heat transfer surface 23A at a temperature higher than the dew point of the reactant gas 32 by allowing the first heating medium 21 to flow through the first heating medium region 2A. The reaction device 100A that includes the heat transfer surface 23A can maintain the catalyst layer 3A at a temperature suitable for the reaction. This allows an increase in efficiency of the reaction.

As illustrated in FIGS. 3 and 4, the second heat exchange section 52A includes a second heat exchange wall 50A and an inner tube 59A. Between the second heat exchange wall 50A and the inner tube 59A, a second heating medium region 5A is provided. The second heating medium region 5A is a region through which the second heating medium 51 flows. The second heat exchange section 52A has a double cylinder structure. The second heating medium 51 in the second heating medium supplying section 57A is supplied into the second heat exchange section 52A through the inner tube 59A. A flow passage between an outer wall surface of the inner tube and an inner wall surface of the second heat exchange wall 50A communicates with an inside of the second heating medium collecting section 58A. The second heating medium 51 that has exited from the second heating medium supplying section 57A and reached an upper end of the inner tube passes through the flow passage and is discharged to the second heating medium collecting section 58A through an outflow port 54A that is provided in an upper wall surface of the second heating medium collecting section 58A.

The second heat exchange wall 50A is made of a member that does not allow any fluid to pass therethrough. A cooling surface 53A (outer surface of the cooling tube) of the second heat exchange wall 50A acts as a second heat exchange surface. The second heat exchange section 52A can maintain the second heat exchange wall 50A and the cooling surface 53A at a temperature not higher than the dew point of the reactant gas 32 by allowing the second heating medium 51 to flow through the second heating medium region 5A.

The catalyst layer 3A is filled with the catalyst 30 that is suitable for the reaction. An area of an upper end of the reaction tube 10A which area excludes an upper end of the catalyst layer 3A is covered with a metallic cap and is provided so that gas cannot flow through the area. In an upper part of the catalyst layer 3A, an opening 38A is provided, through which the source material gas 31 is supplied to the catalyst layer 3A. An upper end of the catalyst layer 3A and the opening 38A need not be flush with each other. A space between the upper end of the catalyst layer 3A and the opening 38A may be filled with a filling 300A. In a lower part of the catalyst layer 3A, an opening 39A is provided. A lower end of the catalyst layer 3A and the opening 39A need not be flush with each other. A space between the lower end of the catalyst layer 3A and the opening 39A may be filled with the filling 300A. The lower end of the catalyst layer 3A is provided with a supporting member that is made of, for example, a metal mesh. The supporting member carries out a function to prevent dropping of the catalyst 30.

The catalyst layer 3A extends in the Z-axis direction and has a height $H_A$ corresponding to the cooling surface 53A having a distance $L_A$. The distance $L_A$ is a distance between the cooling surface 53A and a surface of the catalyst layer 3A which surface is in contact with the inner cylinder 40A. In a case where the cooling surface 53A is an even curved surface in the Z-axis direction, a length of the catalyst layer 3A from its upper end to its lower end can be simply represented by the height $H_A$. In contrast, in a case where the distance $L_A$ is not constant, e.g. in a case where the cooling surface 53A has irregularities in the Z-axis direction, the catalyst layer 3A has a height $H_x$ corresponding to each distance $L_x$. Specifically, the catalyst layer 3 has a height $H_1$ corresponding to a distance $L_1$, a height $H_2$ corresponding to a distance $L_2$ ... a height $H_n$ corresponding to a distance $L_n$. In this case, the length of the catalyst layer 3A from its upper end to its lower end can be represented by a sum total of heights $H_x$ ($H_1+H_2+\ldots+H_n$).

The distance $L_x$ is preferably not less than 0.5 mm and not more than 500 mm. The above range of the distance $L_x$ is preferably achieved in a region of not less than 80%, and more preferably not less than 95% of a vertical length of an entire region obtained by a sum of partial regions of the cooling surface 53A which face the catalyst layer 3A.

The sum total of the heights $H_x$ is preferably not less than 1,000 mm and not more than 20,000 mm. In a case where the sum total is less than 1,000 mm, it is necessary to increase the number of the reaction tubes 10A in order to achieve a sufficient amount of catalyst charged in the reaction device 100A. An increase in number of the reaction tubes 10A leads to, for example, an increase in manufacturing cost. Thus, the above sum total is preferably not less than 1,000 mm from an economic viewpoint. In a case where the above sum total is more than 20,000 mm, it is necessary to manufacture the reaction tubes 10A that are very long and the reaction device 100A that is high. Such reaction tubes 10A and such a reaction device 100A lead to, for example, an increase in manufacturing cost. Thus, the above sum total is preferably not more than 20,000 mm from the economic viewpoint.

The inner cylinder 40A is made of a porous member that allows gas to pass therethrough. The inner cylinder 40A allows gas containing (i) a product produced in the catalyst layer 3A and (ii) an unreacted source material to pass therethrough to the second heat exchange section 52A side.

The space 4A is provided between the inner cylinder 40A and the second heat exchange wall 50A. In Embodiment 2, a condensate flow tube (communicating tube) 42A is provided on a vertically lower side of the space 4A. The condensate flow tube 42A is configured to extend the space 4A vertically downward, and is made of a member that does not allow any liquid to pass therethrough. More specifically, the condensate flow tube 42A forms, between the condensate flow tube 42A and a surface of the second heat exchange section 52A, a space (second space) 6A that is continuous with the space 4A.

On a lower side of a reaction tube 10A, the storing section 48A is provided which stores therein, on the vertically lower side of the space 4A, the condensate 41 that has been produced in the space 4A and the gas that has passed through the catalyst layer 3A. The condensate flow tube 42A is provided inside the storing section 48A, and a lower end of the condensate flow tube 42A is positioned so as to be immersed in the condensate 41 that is stored in a bottom part (referred to as a "condensate storing section 47A") of the storing section 48A.

In a space (referred to as a "gas collection region 49A") on an upper side inside the storing section 48A, an uncondensed gas 32A that has passed through the catalyst layer 3A is stored. The uncondensed gas 32A is a part of the reactant gas 32 which part is discharged after passing through the catalyst layer 3A without being condensed, flowing through the gas collection region 49A (storing section 48A), and coming into contact with the condensate storing section (liquid storing section) 47A. The storing section 48A is provided with an uncondensed gas collection opening 36A (exhaust part) through which the uncondensed gas 32A that is stored in the gas collection region 49A is discharged. The uncondensed gas collection opening 36A is provided at a position vertically above the lower end of the condensate flow tube 42A.

The condensate 41, which is a product that has been condensed in the space 4A, passes through an inside of the condensate flow tube 42A and is discharged to the condensate storing section 47A. The condensate 41 in the condensate storing section 47A is collected through a condensate collection opening 46A that is provided near the bottom part of the storing section 48A. In so doing, discharge of a fluid through the condensate collection opening 46A is controlled so that the reactant gas 32 is prevented from being collected through the condensate collection opening 46A.

(Cumulative Value)

According to the reaction device 100A of Embodiment 2, a cumulative value is not less than 500 mm$^2$, the cumulative value being obtained by cumulatively adding products of the distance $L_x$ and the height $H_x$ from one end to the other end of the cooling surface 53A in a height direction. In a case where the reaction device 100A is a multitube reactor including the plurality of reaction tubes 10A, the cumulative value is not less than 500 mm$^2$ for each of the plurality of reaction tubes 10A.

In the present invention, "a cumulative value obtained by cumulative addition from one end to the other end of the cooling surface 53A in a predetermined direction is not less than 500 mm$^2$" means that a cumulative value obtained by cumulative addition from one end to the other end of the cooling surface 53A in the Z-axis direction only needs to be not less than 500 mm$^2$ at one or more predetermined places. In a case where the cumulative value varies in value depending on a predetermined position in the X-axis direction, the cumulative value obtained by cumulative addition from one end to the other end of the cooling surface 53A in the Z-axis direction can be not less than 500 mm$^2$ in not less than 50%, preferably not less than 80%, more preferably not less than 95%, and particularly preferably 100% of a region in the X-axis direction. Note that the X-axis direction in Embodiment 2 means a circumferential direction of the cooling surface 53A that is cylindrical.

The inventors of the present invention have experimentally found the following. Specifically, in a case where a cumulative value obtained by cumulative addition from one end to the other end of the cooling surface 53A in the Z-axis direction is not less than 500 mm$^2$ at one or more predetermined places in the circumferential direction of the cooling surface 53A that is cylindrical, the reaction device 100A can further improve a reaction yield of a product as compared with a reaction device in which the cumulative value is less than 500 mm$^2$ in 100% of a circumferential region of the cooling surface 53A that is cylindrical, also in the case of using condition parameters identical to those used in the reaction device. The condition parameters include a pressure in a reaction system, a temperature in the reaction system, and a ratio (W/F) between a catalyst amount and a source material feed rate in the reaction system.

In a case where an internal structure of a conventional reaction device is changed so that the cumulative value is not less than 500 mm$^2$, such a change can be achieved by, for example, increasing a diameter of the inner cylinder 40A without changing a diameter of the outer cylinder 20A. First, a case is considered where an amount of the catalyst 30 charged and a density of the catalyst 30 (dilution ratio of the catalyst 30) in the catalyst layer 3A are constant. In this case, in a reaction tube 10A, increasing the diameter of the inner cylinder 40A accordingly increases the sum total of the heights $H_x$ of the catalyst layer 3A. This makes it possible to achieve the reaction device 100A in which the cumulative value is not less than 500 mm$^2$. Such a change is, in other words, a change that increases an area of a part in which the catalyst layer 3A and the inner cylinder 40A are in contact with each other.

In the above reaction, in which the product is condensed and collected out of a reaction container so that the chemical equilibrium is shifted toward the product, any of (i) a reaction rate of a reaction that occurs in the catalyst layer 3A, (ii) a diffusion rate at which the product diffuses toward the cooling surface 53A, and (iii) a condensation rate on the cooling surface 53A governs an entire reaction rate. In a case where the entire reaction rate is controlled by the diffusion rate, increasing the distance $L_x$ is considered to reduce a driving force by which the chemical equilibrium is shifted toward the product, and reduce the entire reaction rate. Thus, a change to increase the distance $L_x$ is commonly not made. However, the inventors of the present invention have experimentally found that the reaction device 100A the internal structure of which is configured such that the cumulative value is not less than 500 mm$^2$ can rather improve the reaction yield of the product.

Furthermore, a change in internal structure such that the cumulative value is not less than 500 mm$^2$ can be achieved also by increasing the sum total of the heights $H_x$. It is possible to increase the sum total of the heights $H_x$ by, for example, diluting the catalyst 30 in the catalyst layer 3A. In order to further increase the cumulative value, it is possible to increase the diameter of the inner cylinder 40A and dilute the catalyst 30.

As described earlier, from the economic viewpoint, the distance $L_x$ is preferably not more than 500 mm, and the sum total of the heights $H_x$ is preferably not more than 20,000 mm. The cumulative value is therefore preferably not more than 10,000,000 mm$^2$.

(Flow of Reaction)

The source material gas 31 is supplied through a source material gas inlet 35A, and is supplied to the catalyst layer 3A in the reaction tube 10A through the opening 38A. The source material gas 31 comes into contact with the catalyst 30 in the catalyst layer 3A, so that a reaction proceeds. The reactant gas 32 that has been produced by the reaction passes through the inner cylinder 40A and travels to the space 4A, and is cooled, on the cooling surface 53A, to a temperature not higher than the dew point of the reactant gas 32, so that a product is condensed. The product that has been condensed and liquefied passes through the space 4A and the condensate flow tube 42A, and drops into the condensate storing section 47A. The condensate 41 that is stored in the condensate storing section 47A is collected through the condensate collection opening 46A.

The reactant gas 32 that passes through the inner cylinder 40A from the catalyst layer 3A side also includes an unreacted source material gas. However, a main component contained in the unreacted source material gas is not condensed on the cooling surface 53A. Furthermore, since the lower end of the condensate flow tube 42A is immersed in the condensate 41 that is stored in the condensate storing section 47A, the unreacted source material gas that moves inside the condensate flow tube 42A is prevented by a liquid surface of the condensate 41 from moving forward, and returns to the catalyst layer 3A. The gas collection region 49A is under a predetermined pressure due to injection of the source material gas 31, and the liquid surface of the condensate 41 in the condensate storing section 47A is also under the predetermined pressure. As such, the liquid surface prevents the unreacted source material gas from being discharged from the lower end of the condensate flow tube 42A without returning to the catalyst layer 3A. Note here that a liquid level $h_A$ in the condensate storing section 47A is desirably maintained in a range that satisfies the following relationship.

$$h_A = \alpha \Delta P / \rho g$$

$$1.0 < \alpha < 10$$

$h_A$: Liquid level in storing section [m]
$\Delta P$: Pressure loss of reactant gas passing through catalyst layer [Pa]
$\rho$: Density of condensate [kg/m$^3$]
g: Gravitational acceleration (=9.8 [m/s$^2$])
$\alpha$: Coefficient [–]

In a case where $h_A$ is too low, some of the reactant gas may pass through the space 4A and the condensate storing section 47A and flow out through the condensate collection opening 46A together with the condensate. This may reduce an efficiency of contact with the catalyst 30. In a case where $h_A$ is too great, the reaction container may have a greater height, and the space 4A may have a higher pressure than the catalyst layer 3A. This may prevent transfer of the product from the catalyst layer 3A to the space 4A.

The uncondensed gas 32A that contains a source material which has not been reacted in the catalyst layer 3A is collected into the gas collection region 49A and collected through the uncondensed gas collection opening 36A that is provided in an upper part of the storing section 48A.

(Collection of Heat of Reaction and Heat of Condensation)

The first heating medium 21 is supplied to the first heat exchange section 22A through the first heating medium feed opening 25A. Heat of reaction which heat has been generated in the catalyst layer 3A is heat exchanged through the outer cylinder 20A and collected by the first heating medium 21. The first heating medium 21 passes through the first heating medium collection opening 26A and is collected into a high-pressure steam separator drum (not illustrated). Then, high-pressure steam obtained by gas-liquid separation is used as, for example, a power source for compressing the source material.

The second heating medium 51 is supplied to the second heating medium supplying section 57A through a second heating medium feed opening 55A, and then is supplied to the second heat exchange section 52A. The second heating medium 51 carries out heat exchange through the second heat exchange wall 50A so as to reduce, on the cooling surface 53A, a temperature of the reactant gas 32 in the space 4A to not higher than the dew point and collect heat of the reactant gas 32. The second heating medium 51 passes through a second heating medium collection opening 56A and is collected into a low-pressure steam separator drum (not illustrated). Then, low-pressure steam obtained by gas-liquid separation is used as, for example, a heat source in a step of purifying the product.

Effect of Embodiment 2

As described above, the reaction device 100A includes the reaction container 1A including at least one reaction tube 10A that has a multiple structure and that causes a reaction, a product of which contains a component having a boiling point higher than a component of a source material gas, and progress of which in a gaseous phase is restricted by a chemical equilibrium between a source material and the product, to proceed inside the at least one reaction tube. Each of the at least one reaction tube 10A includes: the inner cylinder 40A which extends in the Z-axis direction and which allows the reactant gas 32 that has been produced by the reaction to pass therethrough; the outer cylinder 20A inside which the inner cylinder 40A is provided; the second heat exchange section 52A (cooling tube) which is provided inside the inner cylinder 40A; and the catalyst layer 3A which is provided between the inner cylinder 40A and the outer cylinder 20A. A cumulative value is not less than 500 mm$^2$, the cumulative value being obtained by cumulatively adding, from one end to the other end of the cooling surface 53A in the height direction, products of (i) the distance $L_x$ between the cooling surface 53A and the surface of the catalyst layer 3A which surface is in contact with the inner cylinder 40A and (ii) the height $H_x$ of the catalyst layer 3A corresponding to the cooling surface 53A having the distance $L_x$. A temperature of the cooling surface 53A is maintained at a temperature not higher than the dew point of the reactant gas 32, and some of the product is condensed in the space 4A that is provided between the second heat exchange section 52A and the inner cylinder 40A.

According to the reaction device 100A and a chemical reaction method in which the reaction device 100A is used, the product is collected, as the condensate 41, out of the reaction device 100A. This allows the reaction to proceed beyond an equilibrium conversion rate.

Furthermore, according to the reaction device 100A, the cumulative value obtained by cumulative addition from one end to the other end of the cooling surface 53A in the Z-axis direction is not less than 500 mm$^2$ at one or more predetermined places in the circumferential direction of the cooling surface 53A that is cylindrical. Thus, the reaction device 100A and the chemical reaction method in which the reaction device 100A is used can further improve the reaction yield of the product as compared with a reaction device in which the cumulative value is less than 500 mm$^2$ in 100% of a region in the circumferential direction of the cooling surface 53A that is cylindrical.

Embodiment 3

The following description will discuss a further embodiment of the present invention. In Embodiment 2, as understood from FIG. 3, the first heating medium 21 for collecting heat of reaction can be used in a greater amount as compared with the second heating medium 51 for collecting heat of condensation. That is, the reaction device 100A of Embodiment 2 has a configuration that is advantageous in a reaction system in which removal of heat of reaction is important.

In contrast, a reaction device 100B of Embodiment 3 (described below in detail) has a configuration that is advantageous in a reaction system in which removal of heat of condensation is important. The reaction device 100B has a basic principle identical to that of the reaction device 100A.

As in the case of the reaction device 100, the reaction device 100B can be suitably used as a device for carrying out a chemical reaction in which a source material gas 31 contains a carbon oxide and hydrogen and a product of which contains methanol. In addition, the reaction device 100B can be used also for carrying out a reaction that yields dimethyl ether or ammonia as a product.

Figure 5:
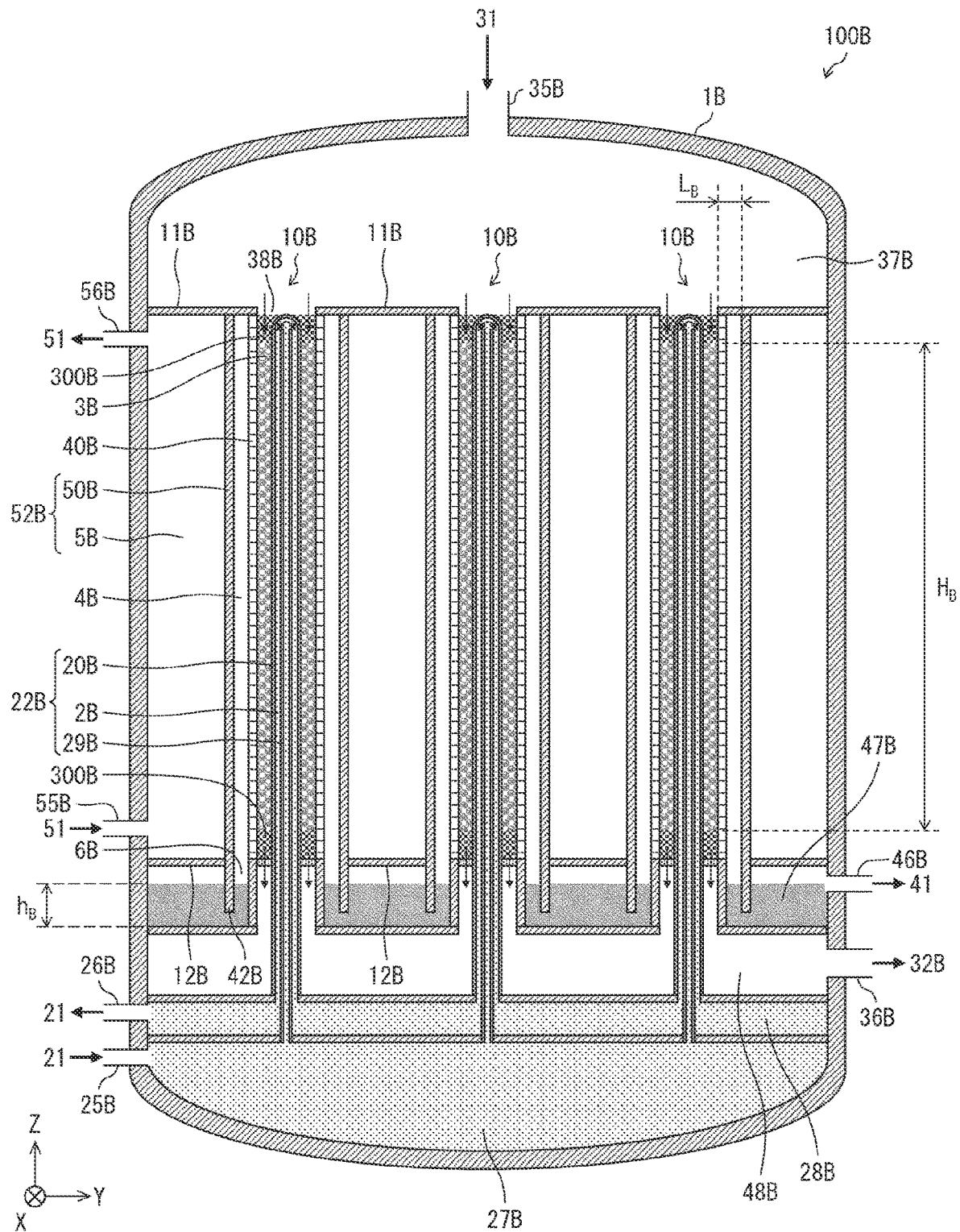
FIG. 5 is a cross-sectional view of a reaction device in accordance with Embodiment 3.
Figure 6:
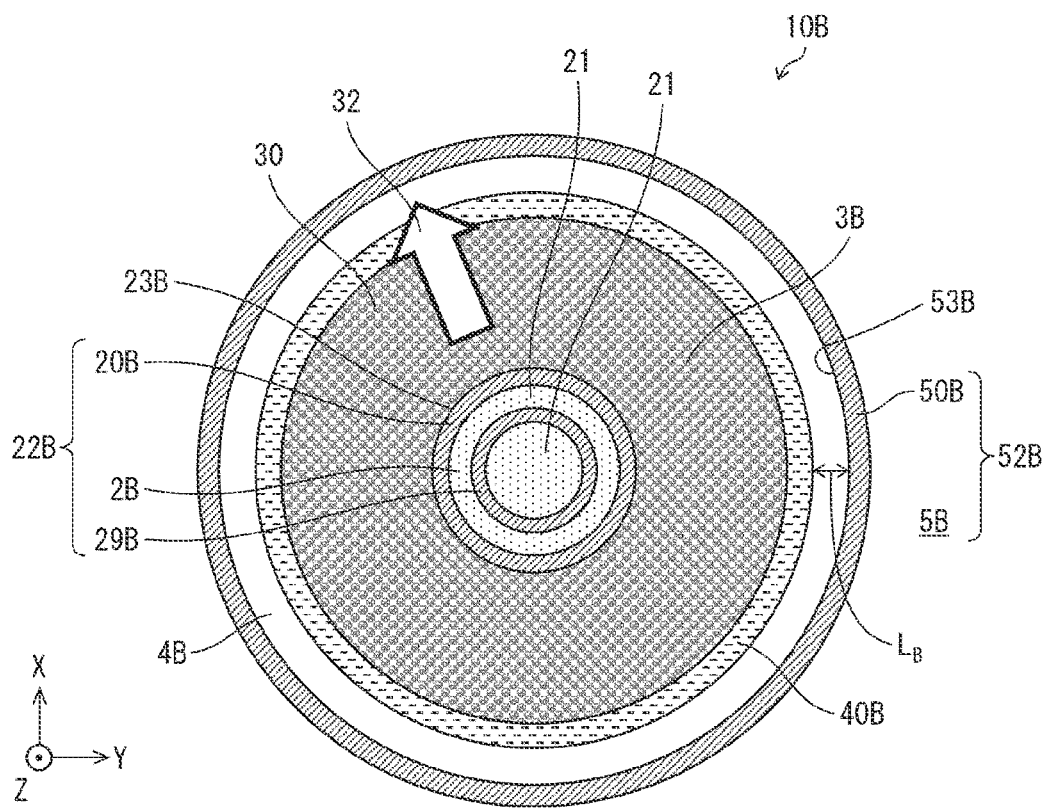
FIG. 6 is a cross-sectional view of a reaction tube included in the reaction device in accordance with Embodiment 3.

FIG. 5 is a cross-sectional view of the reaction device 100B, the cross-sectional view being taken along a plane perpendicular to a bottom surface of the reaction device 100B. FIG. 6 is a cross-sectional view of a reaction tube 10B included in the reaction device 100B, the cross-sectional view being taken along a plane perpendicular to a long axis of the reaction tube 10B.

(Reaction Device 100B)

As illustrated in FIGS. 5 and 6, the reaction device 100B includes a plurality of reaction tubes 10B that are provided inside a reaction container 1B. The number of the reaction tubes 10B that are provided inside the reaction container 1B is not particularly limited, provided that the number is at least one. In consideration of reaction efficiency, the number of the reaction tubes 10B is preferably more than one. On an upper side of the plurality of reaction tubes 10B, a source material gas supplying section 37B is provided which is filled with the source material gas 31 to be supplied to each of the reaction tubes 10B. On a lower side of the plurality of reaction tubes 10B, a condensate storing section 47B (liquid storing section) is provided which stores therein a liquid that has been condensed inside each of the reaction tubes 10B. On a lower side of the condensate storing section 47B, a gas collecting section 48B is provided which stores therein gas that has passed through a catalyst layer 3B. On a lower side of the gas collecting section 48B, a first heating medium collecting section 28B is provided which stores therein a first heating medium 21 that has been discharged from a first heat exchange section 22B (described later). Furthermore, on a lower side of the first heating medium collecting section 28B, a first heating medium supplying section 27B is provided which stores therein the first heating medium 21 to be supplied to the first heat exchange section 22B. The above sections are formed by using a metal plate (e.g. a plate made of stainless steel) to partition an internal space of the reaction container 1B.

The reaction tube 10B includes, in this order from outside, an outer cylinder 50B, an inner cylinder 40B that is provided apart from an inner wall surface of the outer cylinder 50B with a space 4B (first space) between the inner cylinder 40B and the inner wall surface of the outer cylinder 50B, the catalyst layer 3B that has a cylindrical shape and is in contact with an inner wall surface of the inner cylinder 40B, and the first heat exchange section 22B (heat source) that is provided inside the catalyst layer 3B. The catalyst layer 3B and the catalyst layer 3A are similar in material and structure. The inner cylinder 40B, which allows a reactant gas 32 to pass therethrough, and the inner cylinder 40A are similar in material and structure.

A second heat exchange section 52B is a heat exchanger that is constituted by (i) some of an inner wall surface of the reaction container 1B, (ii) an outer wall surface of the outer cylinder 50B, and (iii) metal plates 11B and 12B. Inside the second heat exchange section 52B, a second heating medium region 5B is provided which is common among the plurality of reaction tubes 10B. Through the second heating medium region 5B, the second heating medium 51 flows. The outer cylinder 50B is made of a member that does not allow any fluid to pass therethrough. A cooling surface 53B of the outer cylinder 50B (an inner surface of the outer cylinder 50B) acts as a second heat exchange surface.

The reaction container 1B has a side wall that is provided with (i) a second heating medium feed opening 55B through which the second heating medium 51 is to be supplied to the second heating medium region 5B and (ii) a second heating medium collection opening 56B through which the second heating medium 51 is to be discharged from the second heating medium region 5B. The second heat exchange section 52B can maintain the outer cylinder 50B and the cooling surface 53B at a temperature not higher than a dew point of the reactant gas 32 by allowing the second heating medium 51 to flow through the second heating medium region 5B.

As illustrated in FIGS. 5 and 6, the first heat exchange section 22B is a heat exchanger that includes a first heat exchange wall 20B and an inner tube 29B and that has a heat transfer surface 23B on the catalyst layer 3B side. Between the first heat exchange wall 20B and the inner tube 29B, a first heating medium region 2B is provided. The first heating medium region 2B is a region through which the first heating medium 21 flows.

The first heat exchange section 22B has a double cylinder structure. The first heating medium 21 in the first heating medium supplying section 27B is supplied into the first heat exchange section 22B through the inner tube 29B. A flow passage between an outer wall surface of the inner tube 29B and an inner wall surface of the first heat exchange wall 20B communicates with an inside of the first heating medium collecting section 28B. The first heating medium 21 that has passed through an inside of the inner tube 29B passes through the flow passage, and is discharged to the first heating medium collecting section 28B through an outflow port 24B that is provided in an upper wall surface of the first heating medium collecting section 28B.

The catalyst layer 3B extends in the Z-axis direction and has a height $H_B$ corresponding to the cooling surface 53B having a distance LB. The distance $L_B$ is a distance between the cooling surface 53B and a surface of the catalyst layer 3B which surface is in contact with the inner cylinder 40B. The distance $L_B$, a distance $L_x$, the height $H_B$, and a length from an upper end to a lower end of the catalyst layer 3B (a sum total of heights $H_x$) are similar to those of Embodiment 2. The distance $L_x$ is preferably not less than 0.5 mm and not more than 500 mm. The above range of the distance $L_x$ is preferably achieved in a region of not less than 80%, and more preferably not less than 95% of a vertical length of an entire region obtained by a sum of partial regions of the cooling surface 53B which face the catalyst layer 3B.

The space 4B is provided between the inner cylinder 40B and the outer cylinder 50B. In Embodiment 3, the condensate storing section 47B is provided on a vertically lower side of the space 4B. Furthermore, a condensate flow tube 42B (extension tube) is provided inside the condensate storing section 47B so as to extend the outer cylinder 50B vertically downward. A lower end of the condensate flow tube 42B is positioned so as to be immersed in a condensate 41 that is stored in the condensate storing section 47B. The condensate flow tube 42B forms, inside the condensate storing section 47B, a space (second space) 6B that is continuous with the space 4B.

A liquid that has been condensed in the space 4B (the condensate 41) passes through the space 6B on an inner side of the condensate flow tube 42B and is stored in the condensate storing section 47B. The condensate 41 that is stored in the condensate storing section 47B is collected through a condensate collection opening 46B. In so doing, discharge of a fluid through the condensate collection opening 46B is controlled so that the reactant gas 32 is prevented from being collected through the condensate collection opening 46B.

On a vertically lower side of the catalyst layer 3B, the gas collecting section 48B (gas storing section) is provided into which gas that has passed through the catalyst layer 3B flows. The gas collecting section 48B is provided with an uncondensed gas collection opening 36B (exhaust part).

The condensate storing section 47B and the gas collecting section 48B thus form respective spaces. The condensate storing section 47B forms a closed space with respect to gas. As such, the source material gas 31 that has descended through the space 4B has nowhere to go and consequently returns to the catalyst layer 3B. This makes it possible to reduce the possibility that the source material gas 31 will pass through the space 4B and be discharged externally as it is.

The first heat exchange section 22B is through the gas collecting section 48B, and the inner tube 29B of the first heat exchange section 22B has a lower end that is open to an internal space of the first heating medium supplying section 27B. The flow passage between the outer wall surface of the inner tube 29B and the inner wall surface of the first heat exchange wall 20B communicates with the inside of the first heating medium collecting section 28B. The first heating medium 21 that has exited from the first heating medium supplying section 27B and reached an upper end of the inner tube 29B passes through the flow passage and is discharged to the first heating medium collecting section 28B through the outflow port 24B that is provided in the upper wall surface of the first heating medium collecting section 28B.

(Cumulative Value)

According to the reaction device 100B of Embodiment 3, a cumulative value is not less than 500 mm², the cumulative value being obtained by cumulatively adding products of the distance $L_x$ and a height $H_x$ from one end to the other end of the cooling surface 53B in a height direction. In a case where the reaction device 100B is a multitube reactor including the plurality of reaction tubes 10B, the cumulative value is not less than 500 mm² for each of the plurality of reaction tubes 10B.

In the present invention, "a cumulative value obtained by cumulative addition from one end to the other end of the cooling surface 53B in a predetermined direction is not less than 500 mm²" means that a cumulative value obtained by cumulative addition from one end to the other end of the cooling surface 53B in the Z-axis direction only needs to be not less than 500 mm² at one or more predetermined places.

In a case where the cumulative value varies in value depending on a predetermined position in the X-axis direction, the cumulative value obtained by cumulative addition from one end to the other end of the cooling surface 53B in the Z-axis direction can be not less than 500 mm² in not less than 50%, preferably not less than 80%, more preferably not less than 95%, and particularly preferably 100% of a region in the X-axis direction. Note that the X-axis direction in Embodiment 3 means a circumferential direction of the cooling surface 53B that is cylindrical.

In a case where an internal structure of a conventional reaction device is changed so that the cumulative value is not less than 500 mm², such a change can be achieved by, for example, decreasing a diameter of the inner cylinder 40B. First, a case is considered where an amount of the catalyst 30 charged and a density of the catalyst 30 (dilution ratio of the catalyst 30) in the catalyst layer 3B are constant. In this case, in a reaction tube 10B, decreasing the diameter of the inner cylinder 40B accordingly increases the sum total of the heights $H_x$ of the catalyst layer 3B. This makes it possible to achieve the reaction device 100B in which the cumulative value is not less than 500 mm². Such a change is, in other words, a change that increases an area of a part in which the catalyst layer 3B and the inner cylinder 40B are in contact with each other.

Furthermore, a change in internal structure such that the cumulative value is not less than 500 mm² can be achieved also by, for example, diluting the catalyst 30 in the catalyst layer 3B. In order to further increase the cumulative value, it is possible to increase the diameter of the inner cylinder 40B and dilute the catalyst 30.

As described earlier, from the economic viewpoint, the distance $L_x$ is preferably not more than 500 mm, and the sum total of the heights $H_x$ is preferably not more than 20,000 mm. The cumulative value is therefore preferably not more than 10,000,000 mm².

(Flow of Reaction)

The source material gas 31 is supplied through a source material gas inlet 35B, and is supplied to the catalyst layer 3B in the reaction tube 10B through an opening 38B. The source material gas 31 comes into contact with the catalyst 30 in the catalyst layer 3B, so that a reaction proceeds. The reactant gas 32 that has been produced by the reaction passes through the inner cylinder 40B and travels to the space 4B, and is cooled, on the inner wall surface (second heat exchange surface) of the outer cylinder 50B, to a temperature not higher than the dew point of the reactant gas 32, so that a product is condensed. The product that has been condensed and liquefied passes through the space 4B and drops into the condensate storing section 47B. The condensate 41 that is stored in the condensate storing section 47B is collected through the condensate collection opening 46B.

The reactant gas 32 that passes through the inner cylinder 40B from the catalyst layer 3B side toward the outer cylinder 50B also includes an unreacted source material gas. However, a main component contained in the unreacted source material gas is not condensed in the outer cylinder 50B. Furthermore, since the condensate storing section 47B forms a closed space with respect to gas, the unreacted source material gas that has descended through the space 4B has nowhere to go and is prevented by a liquid surface of the condensate 41 from moving forward. Thus, the unreacted source material gas returns to the catalyst layer 3B. Note here that a liquid level hs in the condensate storing section 47B is desirably maintained in a range that satisfies the following relationship.

$$hB = \alpha \Delta P / \rho g$$

$$1.0 < \alpha < 10$$

hB: Liquid level in storing section [m]

ΔP: Pressure loss of reactant gas passing through catalyst layer [Pa]

ρ: Density of condensate [kg/m³]

g: Gravitational acceleration (=9.8 [m/s²])

α: Coefficient [–]

In a case where $h_B$ is too low, some of the reactant gas 32 may pass through the space 4B and the condensate storing section 47B and flow out through the condensate collection opening 46B together with the condensate. This may reduce an efficiency of contact with the catalyst 30. In a case where $h_B$ is too great, the reaction container may have a greater height, and the space 4B may have a higher pressure than the catalyst layer 3B. This may prevent mass transfer of the product from the catalyst layer 3B to the space 4B.

An uncondensed gas 32B that contains a source material which has descended through the catalyst layer 3B without being reacted in the catalyst layer 3B is collected into the gas collection section 48B and collected through the uncondensed gas collection opening 36B that is provided in the gas collecting section 48B.

(Collection of Heat of Reaction and Heat of Condensation)

The first heating medium 21 is supplied to the first heating medium supplying section 27B through a first heating medium feed opening 25B, and then is supplied to the first heat exchange section 22B. Heat of reaction which heat has been generated in the catalyst layer 3B is heat exchanged through the first heat exchange wall 20B and collected by the first heating medium 21. The first heating medium 21 passes through a first heating medium collection opening 26B and is collected into a high-pressure steam separator drum (not illustrated). Then, high-pressure steam obtained by gas-liquid separation is used as, for example, a power source for compressing the source material.

The second heating medium 51 is supplied to the second heat exchange section 52B through the second heating medium feed opening 55B. The second heating medium 51 carries out heat exchange through the outer cylinder 50B so as to reduce a temperature of the reactant gas 32 in the space 4B to not higher than the dew point and collect heat of the reactant gas 32. The second heating medium 51 passes through the second heating medium collection opening 56B and is collected into a low-pressure steam separator drum (not illustrated). Then, low-pressure steam obtained by gas-liquid separation is used as, for example, a heat source in a step of purifying the product.

Effect of Embodiment 3

As described above, the reaction device 100B includes the reaction container 1B including at least one reaction tube 10B that has a multiple structure and that causes a reaction, a product of which contains a component having a boiling point higher than a component of the source material gas 31, and progress of which in a gaseous phase is restricted by a chemical equilibrium between a source material and the product, to proceed inside the at least one reaction tube. Each of the at least one reaction tube 10B includes: the inner cylinder 40B which extends in the Z-axis direction and which allows the reactant gas 32 that has been produced by the reaction to pass therethrough; the outer cylinder 50B inside which the inner cylinder 40B is provided; and the catalyst layer 3B which is provided inside the inner cylinder 40B. A cumulative value is not less than 500 mm², the cumulative value being obtained by cumulatively adding, from one end to the other end of the cooling surface 53B in the Z-axis direction, products of (i) the distance $L_x$ between the cooling surface 53B and the surface of the catalyst layer 3B which surface is in contact with the inner cylinder 40B and (ii) the height $H_x$ of the catalyst layer 3B corresponding to the cooling surface 53B having the distance $L_x$. A temperature of the cooling surface 53B of the outer cylinder 50B is maintained at a temperature not higher than the dew point of the reactant gas 32, and some of the product is condensed in the space 4B that is provided between the outer cylinder 50B and the inner cylinder 40B.

According to the reaction device 100B and a chemical reaction method in which the reaction device 100B is used, the product is collected, as the condensate 41, out of the reaction device 100B. This allows the reaction to proceed beyond an equilibrium conversion rate.

Furthermore, according to the reaction device 100B, the cumulative value obtained by cumulative addition from one end to the other end of the cooling surface 53B in the Z-axis direction is not less than 500 mm² at one or more predetermined places in the circumferential direction of the cooling surface 53B that is cylindrical. Thus, the reaction device 100B and the chemical reaction method in which the reaction device 100B is used can improve a reaction yield of the product also in the case of using condition parameters identical to those used in a reaction device in which the cumulative value is less than 500 mm² in 100% of a region in the circumferential direction of the cooling surface 53B that is cylindrical.

(Comparative Example and Examples 1 to 5)

(Verification Test)

Figure 7:
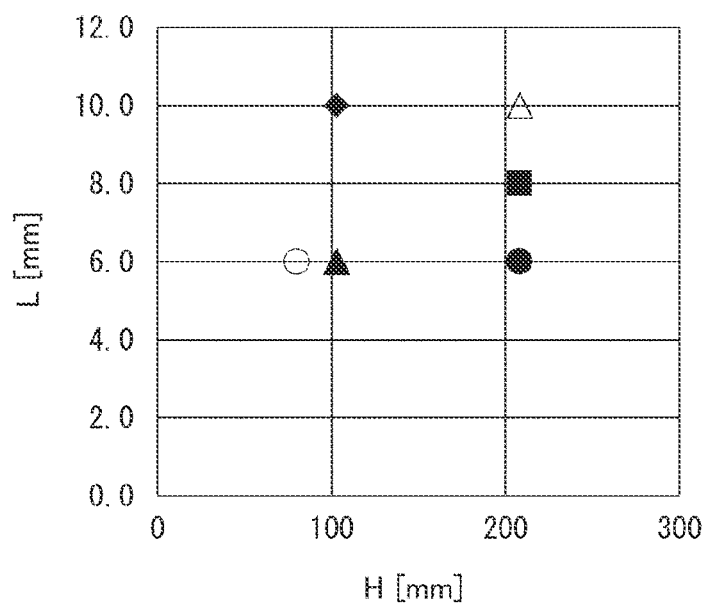
FIG. 7 is a graph showing a diagram of relationship between a distance L and a height H for Comparative Example and Examples 1 to 5.
Figure 8:
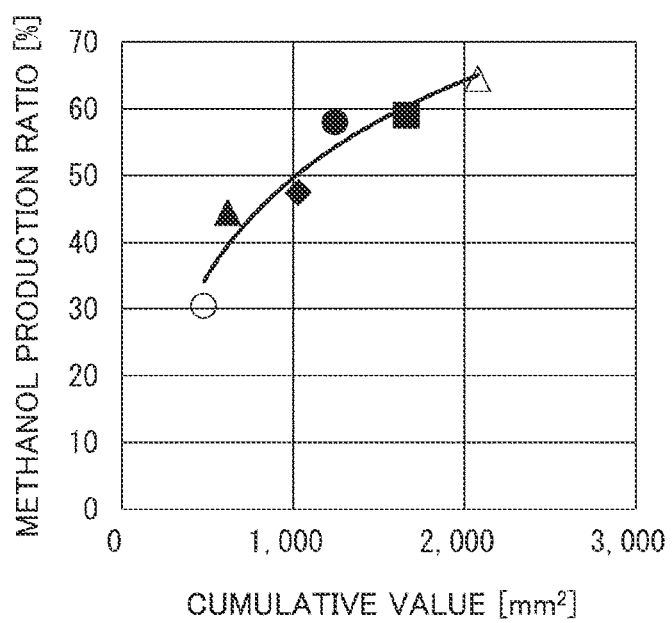
FIG. 8 is a graph showing a relationship between (a) a cumulative value of products of the distance L and the height H and (b) a methanol production ratio for Comparative Example and Examples 1 to 5.

In the present verification test, the reaction device 100A described in Embodiment 2 was used to carry out a methanol synthesis reaction in order to investigate a relationship between the cumulative value and a methanol production ratio. An example in which an internal configuration was employed such that the cumulative value is less than 500 mm² in 100% of a region in a circumferential direction of a cylindrical cooling surface is regarded as a comparative example. Table 1 shows conditions of internal configurations of Comparative Example and Examples 1 to 5 and obtained results. FIG. 7 is a graph showing a relationship between a distance $L_A$ and a height $H_A$ for Comparative Example and Examples 1 to 5. FIG. 8 is a graph showing a relationship between the cumulative value and a methanol production ratio for Comparative Example and Examples 1 to 5. Condition parameters unified between Comparative Example and Examples 1 to 5 in the present verification test are as follows.

Source material flow rate . . . 115 [Ncc/min]

Source material gas composition: $H_2$ 72%, $CO_2$ 24%, $N_2$ 4%

Catalyst: "Copper based methanol synthesis catalyst" purchased from Alfa Aesar

Amount of catalyst charged . . . 122 [g]

Ratio (W/F) between catalyst amount and source material feed rate . . . 412 [g/(mol/h)]

Pressure . . . 0.85 [MPaG]

Reaction temperature . . . 240 [° C.]

Cooling water temperature . . . –10 [° C.]

Table 1 below shows conditions of Comparative Example and Examples.

TABLE 1

|  | Comparative Example ○ | Example 1 ▲ | Example 2 ◆ | Example 3 ● | Example 4 ■ | Example 5 △ |
|---|---|---|---|---|---|---|
| L [mm] | 6.0 | 6.0 | 10.0 | 6.0 | 8.0 | 10.0 |
| H [mm] | 80 | 103 | 103 | 208 | 208 | 208 |
| Catalyst dilution ratio [fold] | 1.0 | 1.3 | 1.0 | 2.6 | 2.3 | 2.0 |
| Cumulative value [mm²] | 480 | 618 | 1,030 | 1,248 | 1,664 | 2,080 |
| Methanol production ratio [%] | 30.4 | 44.5 | 47.5 | 58.0 | 59.0 | 64.5 |

In Examples 1 and 3, the cumulative value was increased by increasing the height H by diluting the catalyst 30, as compared with Comparative Example. In Example 2, the cumulative value was increased by increasing the distance L, as compared with Example 1. In Examples 4 and 5, the cumulative value was further increased by not only increasing the distance L but also increasing the height H by diluting the catalyst 30, as compared with Example 1.

As illustrated in FIG. 8, it is understood that Examples in which the cumulative value is not less than 500 mm² each have achieved a higher methanol production ratio as compared with Comparative Example in which the cumulative value is less than 500 mm² in 100% of a region in the circumferential direction of the cylindrical cooling surface. It is also understood from FIG. 7 that a higher cumulative value results in a higher methanol production ratio.

That is, it has been verified that, also in a case where the condition parameters are unified, a yield of a product can be increased by changing an internal structure so that the cumulative value is not less than 500 mm².

(Other Examples)

Examples 6 and 7 below, in which condition parameters differ from those in Examples 1 to 5, are within the scope of the present invention. In Examples 6 and 7, the cumulative value is greater than in Examples 1 to 5.

(Example 6)

The condition parameters in Example 6 are as follows. Source material flow rate: 1,000 [Ncc/min]; Source material gas composition: $H_2$ 71%, $CO_2$ 25%, $N_2$ 4%; Catalyst: Purchased from Alfa Aesar "Copper based methanol synthesis catalyst"; Amount of catalyst charged: 1,746 [g]; Catalyst dilution ratio: 1.0 [fold]; Ratio (W/F) between catalyst amount and source material feed rate: 679 [g/(mol/h)]; Pressure: 0.85 [MPaG]; Reaction temperature: 200 [° C.]; Cooling water temperature: −10 [° C.]; Distance L: 7.8 [mm]; Height H: 1,500 [mm]; Cumulative value: 11,700 [mm²] The methanol production ratio was 87.3% in Example 6.

(Example 7)

The condition parameters in Example 7 are as follows. Source material flow rate: 1,000 [Ncc/min]; Source material gas composition: $H_2$ 71%, $CO_2$ 25%, $N_2$ 4%; Catalyst: Purchased from Alfa Aesar "Copper based methanol synthesis catalyst"; Amount of catalyst charged: 2,580 [g]; Catalyst dilution ratio: 1.0 [fold]; Ratio (W/F) between catalyst amount and source material feed rate: 1,003 [g/(mol/h)]; Pressure: 0.85 [MPaG]; Reaction temperature: 200 [° C.]; Cooling water temperature: −10 [° C.]; Distance L: 3.8 [mm]; Height H: 1,500 [mm]; Cumulative value: 5,700 [mm²] The methanol production ratio was 88.1% in Example 7.

REFERENCE SIGNS LIST 1, 1A, 1B . . . Reaction container
3, 3A, 3B . . . Catalyst layer
4, 4, 4B . . . Space
10A, 10B . . . Reaction tube
20A . . . Outer cylinder
23, 23A, 23B . . . Heat transfer surface
30 . . . Catalyst
31 . . . Source material gas
32 . . . Reactant gas
40 . . . Transmission wall
40A, 40B . . . Inner cylinder
50B . . . Outer cylinder
53, 53A, 53B . . . Cooling surface
100, 100A, 100B . . . Reaction device
300, 300A, 300B . . . Filling

The invention claimed is:

1. A chemical reaction method that causes a reaction, a product of which contains a component having a boiling point higher than a component of a source material gas, and progress of which in a gaseous phase is restricted by a chemical equilibrium between a source material and the product, to proceed, wherein
a chemical reaction device including:
a catalyst layer which contains a catalyst that promotes the reaction;
a cooling surface which is provided apart from the catalyst layer with a space between the cooling surface and the catalyst layer, which is maintained at a temperature not higher than a dew point of a reactant gas produced by the reaction, and which extends in a predetermined direction; and
a transmission wall which is provided at a boundary between the catalyst layer and the space and which allows the reactant gas to pass therethrough,
a cumulative value being not less than 500 mm², the cumulative value being obtained by cumulatively adding, from one end to the other end of the cooling surface in the predetermined direction, products of (i) a distance between (a) a surface of the catalyst layer which surface is in contact with the transmission wall and (b) the cooling surface and (ii) a height of the catalyst layer corresponding to the cooling surface having the distance, is used
to cause a chemical reaction to proceed by supplying the source material gas to the catalyst layer, and
to condense, on the cooling surface and in the space, some of a product produced by the chemical reaction.

2. The chemical reaction method as set forth in claim 1, wherein the source material gas contains a carbon oxide and hydrogen, and the product contains methanol.

3. The chemical reaction method as set forth in claim 1, wherein the cumulative value is not more than 10,000,000 mm².

4. A chemical reaction device that causes a reaction, a product of which contains a component having a boiling point higher than a component of a source material gas, and progress of which in a gaseous phase is restricted by a chemical equilibrium between a source material and the product, to proceed, said chemical reaction device comprising:

a catalyst layer to which the source material gas is supplied and which contains a catalyst that promotes the reaction;

a cooling surface which is provided apart from the catalyst layer with a space between the cooling surface and the catalyst layer, which is maintained at a temperature not higher than a dew point of a reactant gas that has been produced by the reaction, and which extends in a predetermined direction; and a transmission wall which is provided at a boundary between the catalyst layer and the space and which allows the reactant gas to pass therethrough, a cumulative value being not less than 500 mm$^2$, the cumulative value being obtained by cumulatively adding, from one end to the other end of the cooling surface in the predetermined direction, products of (i) a distance between (a) a surface of the catalyst layer which surface is in contact with the transmission wall and (b) an outer surface of the cooling surface and (ii) a height of the catalyst layer corresponding to the outer surface having the distance, and the chemical reaction device condensing some of a product on a surface of the cooling surface and in the space.

5. The chemical reaction device as set forth in claim 4, wherein the source material gas contains a carbon oxide and hydrogen, and the product contains methanol.

6. The chemical reaction device as set forth in claim 4, wherein the cumulative value is not more than 10,000,000 mm$^2$.

7. A chemical reaction device as set forth in claim 4, further comprising a heat transfer surface on an opposite side from the transmission wall with the catalyst interposed between the heat transfer surface and the transmission wall, the heat transfer surface being maintained at a higher temperature than the cooling surface.

8. The chemical reaction device as set forth in claim 5, wherein the distance is not less than 0.5 mm and not more than 500 mm, and the height of the catalyst layer is not less than 1,000 mm and not more than 20,000 mm.

9. A chemical reaction device comprising a reaction container including at least one reaction tube that has a multiple structure and that causes a reaction, a product of which contains a component having a boiling point higher than a component of a source material gas, and progress of which in a gaseous phase is restricted by a chemical equilibrium between a source material and the product, to proceed inside the at least one reaction tube, the at least one reaction tube each including:

an inner cylinder which allows a reactant gas produced by the reaction to pass therethrough;

an outer cylinder inside which the inner cylinder is provided;

a cooling tube which is provided inside the inner cylinder and which extends in a predetermined direction; and a catalyst layer which is provided between the inner cylinder and the outer cylinder, a cumulative value being not less than 500 mm$^2$, the cumulative value being obtained by cumulatively adding, from one end to the other end of the cooling tube in the predetermined direction, products of (i) a distance between (a) a surface of the catalyst layer which surface is in contact with the inner cylinder and (b) an outer surface of the cooling tube and (ii) a height of the catalyst layer corresponding to the outer surface having the distance, a temperature of the outer surface of the cooling tube being maintained at a temperature not higher than a dew point of the reactant gas, and the chemical reaction device condensing some of the product in a space provided between the cooling tube and the inner cylinder.

10. The chemical reaction device as set forth in claim 9, wherein the cumulative value is not more than 10,000,000 mm$^2$.

11. A chemical reaction device as set forth in claim 9, further comprising a heating medium in a space defined by an inner wall of the reaction container and an outer wall of the reaction tube.

12. The chemical reaction device as set forth in claim 9, wherein the distance is not less than 0.5 mm and not more than 500 mm, and the height of the catalyst layer is not less than 1,000 mm and not more than 20,000 mm.

13. A chemical reaction device comprising a reaction container including at least one reaction tube that has a multiple structure and that causes a reaction, a product of which contains a component having a boiling point higher than a component of a source material gas, and progress of which in a gaseous phase is restricted by a chemical equilibrium between a source material and the product, to proceed inside the at least one reaction tube, the at least one reaction tube each including:

an inner cylinder which allows a reactant gas produced by the reaction to pass therethrough;

an outer cylinder inside which the inner cylinder is provided and which extends in a predetermined direction; and a catalyst layer which is provided inside the inner cylinder, a cumulative value being not less than 500 mm$^2$, the cumulative value being obtained by cumulatively adding, from one end to the other end of an inner surface of the outer cylinder in the predetermined direction, products of (i) a distance between (a) a surface of the catalyst layer which surface is in contact with the inner cylinder and (b) the inner surface and (ii) a height of the catalyst layer corresponding to the inner surface having the distance, a temperature of the inner surface of the outer cylinder being maintained at a temperature not higher than a dew point of the reactant gas, and the chemical reaction device condensing some of the product in a space provided between the outer cylinder and the inner cylinder.

14. The chemical reaction device as set forth in claim 13, wherein the cumulative value is not more than 10,000,000 mm$^2$.

15. A chemical reaction device as set forth in claim 13, further comprising a heat source inside the catalyst layer.

16. The chemical reaction device as set forth in claim 13, wherein the distance is not less than 0.5 mm and not more than 500 mm, and the height of the catalyst layer is not less than 1,000 mm and not more than 20,000 mm.

17. A methanol production method that causes a reaction, a product of which contains a component having a boiling point higher than a component of a source material gas, and progress of which in a gaseous phase is restricted by a chemical equilibrium between a source material and the product, to proceed, wherein a chemical reaction device containing carbon oxide and hydrogen as the source material gas, the chemical reaction device including:
- a catalyst layer which contains a catalyst for methanol synthesis;
- a cooling surface which is provided apart from the catalyst layer with a space between the cooling surface and the catalyst layer, which is maintained at a temperature not higher than a dew point of a reactant gas produced by the reaction, and which extends in a predetermined direction; and
- a transmission wall which is provided at a boundary between the catalyst layer and the space and which allows the reactant gas to pass therethrough, a cumulative value being not less than 500 $mm^2$, the cumulative value being obtained by cumulatively adding, from one end to the other end of the cooling surface in the predetermined direction, products of (i) a distance between (a) a surface of the catalyst layer which surface is in contact with the transmission wall and (b) the cooling surface and (ii) a height of the catalyst layer corresponding to the cooling surface having the distance, is used to cause a chemical reaction to proceed by supplying the source material gas to the catalyst layer, and to condense, on the cooling surface and in the space, some of a reactant gas produced by the chemical reaction.

\* \* \* \* \*